(12) United States Patent
Jimenez-Carvajal et al.

(10) Patent No.: US 10,518,110 B1
(45) Date of Patent: Dec. 31, 2019

(54) SYSTEMS AND METHODS FOR CALIBRATING AND CONTROLLING COLLIMATOR LEAVES

(71) Applicant: Elekta Limited, West Sussex (GB)

(72) Inventors: Miguel Jimenez-Carvajal, Croydon (GB); Ralf Spriestersbach, West Sussex (GB)

(73) Assignee: Elekta Limited, West Sussex (GB)

( * ) Notice: Subject to any disclaimer, the term of this patent is extended or adjusted under 35 U.S.C. 154(b) by 6 days.

(21) Appl. No.: 16/051,990

(22) Filed: Aug. 1, 2018

(51) Int. Cl.
*A61N 5/10* (2006.01)
*G21K 1/04* (2006.01)

(52) U.S. Cl.
CPC ......... *A61N 5/1075* (2013.01); *A61N 5/1045* (2013.01); *G21K 1/046* (2013.01); *A61N 2005/1074* (2013.01)

(58) Field of Classification Search
CPC .. A61N 5/1042; A61N 5/1045; A61N 5/1075; G21K 1/046
See application file for complete search history.

(56) References Cited

U.S. PATENT DOCUMENTS

| 4,882,741 | A | 11/1989 | Brown |
| 7,020,245 | B2 | 3/2006 | Noguchi |
| 8,467,499 | B2 | 6/2013 | Furth et al. |
| 9,774,838 | B2 * | 9/2017 | Chappelow .......... H04N 5/2254 |
| 9,943,705 | B2 * | 4/2018 | Chappelow .......... A61N 5/1045 |
| 9,950,193 | B2 * | 4/2018 | Chappelow .......... A61N 5/1048 |
| 2009/0196401 | A1 | 8/2009 | Awan et al. |
| 2016/0361567 | A1 * | 12/2016 | Chappelow .......... A61N 5/1048 |
| 2016/0361568 | A1 * | 12/2016 | Chappelow .......... A61N 5/1045 |
| 2016/0366385 | A1 * | 12/2016 | Chappelow .......... H04N 5/2254 |
| 2018/0193671 | A1 * | 7/2018 | Chappelow .......... A61N 5/1045 |

FOREIGN PATENT DOCUMENTS

EP 0314231 A2 5/1989

OTHER PUBLICATIONS

Gribbon, K.T. et al., "A Real-time FPGA Implementation of a Barrel Distortion Correction Algorithm with Bilinear Interpolation," Proceedings of Image and Vision Computing New Zealand Conference, pp. 408-413 (Nov. 2003).

* cited by examiner

*Primary Examiner* — Thomas R Artman
(74) *Attorney, Agent, or Firm* — Finnegan, Henderson, Farabow, Garrett & Dunner, L.L.P.

(57) ABSTRACT

Systems and methods for calibrating and controlling leaves of a multi-leaf collimator are disclosed. According to an exemplary method, a controller may receive images of collimator leaves and may determine a minor offset between an imaging marker and the tip of the respective leaf. In addition, the controller may quantify a barrel distortion effect associated with a leaf-imaging camera. The controller may correct leaf position data using the minor offsets and barrel distortion quantification, and may use the corrected leaf positions to accurately place the leaves during radiotherapy. Advantageously, a desired beam shaping window may be formed with the leaves, ensuring that healthy tissue is minimally irradiated while also ensuring that the target tissue receives the correct radiation dose. Embodiments of the present disclosure provide collimator calibration techniques which may be faster than prior calibration techniques, allowing shortened calibration times and faster radiotherapy sessions.

20 Claims, 14 Drawing Sheets

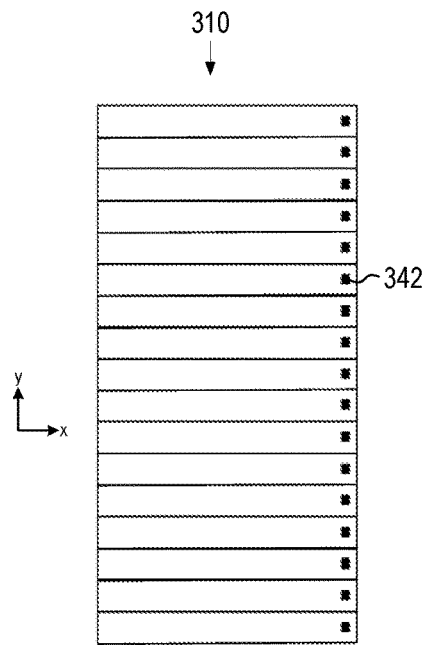
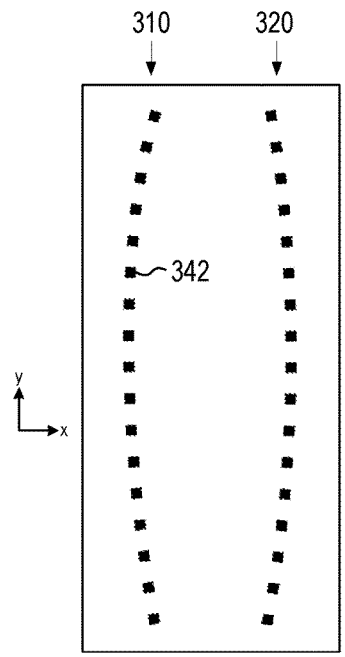
FIG. 4A
FIG. 4B
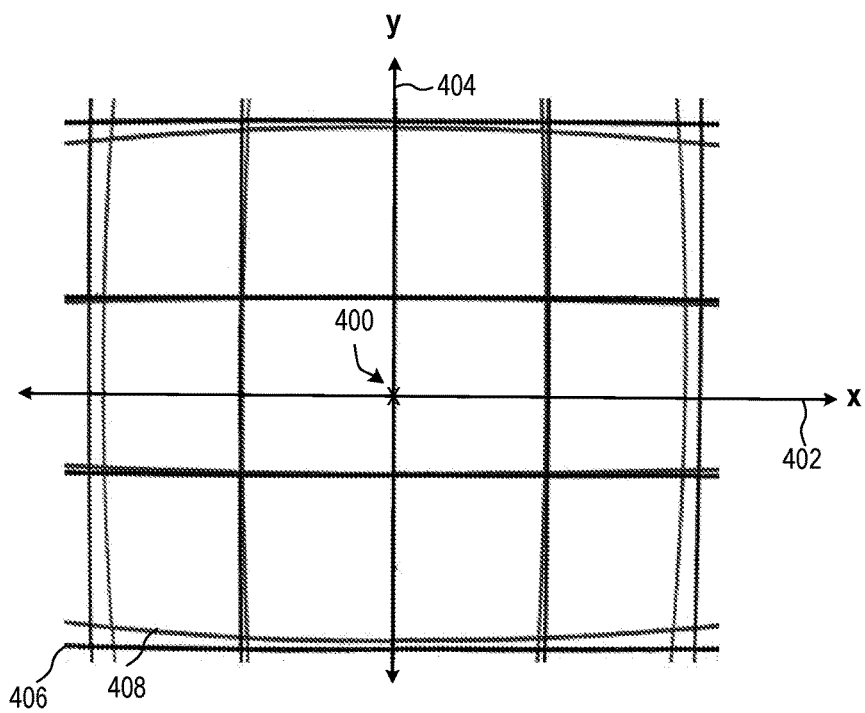
FIG. 4C

SYSTEMS AND METHODS FOR CALIBRATING AND CONTROLLING COLLIMATOR LEAVES

TECHNICAL FIELD

This disclosure relates generally to multi-leaf collimators of radiotherapy systems. More specifically, this disclosure relates to systems and methods for calibrating and controlling movement of leaves of a multi-leaf collimator.

BACKGROUND

Radiotherapy is used to treat cancers and other ailments by irradiating tissue with ionizing radiation. Radiotherapy systems generate a beam of radiation (e.g. electrons, protons, ions, and the like) and direct the beam towards a target site, such as a tumour. To concentrate the radiation at the target site and to minimize irradiation of healthy surrounding tissue, radiotherapy systems often also include a beam-shaping device such as a multi-leaf collimator (MLC). A MLC includes rows of elongate leaves that are arranged side-to-side and constructed of a radiation-shielding material such as tungsten. Each leaf can be independently moved into and out of the path of the radiation to block a portion of the beam. By arranging the collimator leaves, the MLC can be used to shape the radiation beam in order to focus the dose on the target tissues.

Given the importance of accurately controlling the beam shape, techniques have been developed to calibrate the positions of collimator leaves. For example, some radiation-based calibration techniques utilize x-ray film or point dosimeters to confirm that the leaves form the desired radiation beam shape. However, such techniques can be time-consuming and often provide a poor indication of the actual beam geometry. Other calibration techniques involve using a laser beam and optical detector to determine when the MLC leaves have reached a defined calibration position. However, this technique may not provide an accurate indication of the leaf positions for all leaf shape configurations. Still further calibration techniques involve imaging optical markers on the leaves with a camera and using the detected positions of the optical markers to determine the positions of the leaves. However, the lens of the camera can distort the images of the markers, meaning additional calibration steps may be necessary to provide accurate determination of the leaf positions. The extent of this distortion is different for each lens and can change every time adjustments are made to the camera; thus, a distortion correction technique developed for one camera may not be applicable to other cameras, or to the camera in question after servicing. In addition, because the optical markers are manually placed on the collimator leaves, the distance between the marker and the leaf tip (a distance known as the "minor offset") is different for each leaf. Existing MLCs cannot simply measure the minor offset with the camera because the leaves are not visible to the camera. For these reasons, existing collimator systems may require computationally-intensive and time-consuming calibration steps to ensure that collimator leaves are correctly positioned during radiotherapy.

Thus, there remains a need for improved techniques for accurately monitoring collimator leaf positions by minimizing the distortion of leaf images caused by the camera lens and by accurately measuring and accounting for the minor offsets of the leaves in a more timely fashion. The present disclosure provides systems and methods for generating undistorted images of collimator leaves and accurate measurements of the minor offsets using a minimal number of measurements, such that the true positions of the leaves can be determined without adding excessive calibration time to the machine setup process. As a result, the leaves can be even more accurately placed during radiotherapy so that the desired beam geometry can be achieved and the time required to perform the calibration may be reduced.

SUMMARY

Disclosed herein are systems and methods for correcting distortion of images of collimator leaves which is caused by the lens of a leaf-imaging camera, and for accurately measuring the minor offsets of the collimator leaves. Particular examples of the disclosure may enable accurate determination of the positions of the collimator leaves, thus providing more exact positioning of leaves to shape radiation beams during radiotherapy.

According to an exemplary embodiment of the present disclosure, a computer-implemented method for calibrating leaves of a multi-leaf collimator of a radiotherapy device is provided, the leaves including imaging markers and configured to shape a radiation beam emitted by the radiotherapy device by blocking radiation, wherein the radiotherapy device includes an imaging device configured to image the leaves, the imaging device including a lens. The method includes receiving a plurality of images of the leaves from the imaging device. The leaves are in a first position in at least a first image and in a second position in at least a second image. The method further includes generating, based at least in part on the first image and the second image, initial position estimates of the leaves in the first position and in the second position. The initial position estimates of the leaves are generated with respect to a predetermined coordinate space associated with the multi-leaf collimator. The method further includes determining, based at least in part on the initial position estimates of the leaves in the first position and in the second position, offsets for the leaves. The offsets reflect differences between imaging marker positions of the leaves and positions of tips of the leaves. The method further includes identifying first position coordinates, with respect to the predetermined coordinate space, for the leaves based upon the offsets of the leaves and the initial position estimates of the leaves. The method further includes calculating a distortion coefficient of the lens based upon the first position coordinates for the leaves and the offsets of the leaves. The distortion coefficient reflects an optical distortion effect associated with the lens. The method further includes determining corrected position coordinates, with respect to the predetermined coordinate space, for the leaves based on the distortion coefficient and the first position coordinates for the leaves. The method further includes correcting the offsets for the leaves based on the corrected position coordinates for the leaves. The method further includes calibrating the multi-leaf collimator based on the corrected offsets, wherein at least one leaf of the multi-leaf collimator is controlled based on the calibration.

The multi-leaf collimator includes two banks of leaves which are captured in the images. Two opposing leaves constitute a leaf pair. The first position is a retracted position of the leaves and the second position is an extended position of the leaves. A first bank of leaves moves into the retracted position in the first image and the extended position in the second image. A second bank of leaves moves into the extended position in the first image and the retracted position in the second image. Calculating the distortion coefficient includes identifying, in the predetermined coordinate space, a lens x-coordinate and a lens y-coordinate associated with a centre of the lens. Identifying the lens x-coordinate includes, for each leaf pair, generating a function based on the first position coordinates of the two opposing leaves in the first position and in the second position. Identifying the lens x-coordinate additionally includes identifying a maximum or a minimum of each function; determining an x-coordinate, relative to the predetermined coordinate space, of each maximum or minimum; and averaging the x-coordinates of the maximums and minimums. The function of each leaf pair is a second-order polynomial. Identifying the lens y-coordinate includes generating, for each bank of leaves in each of the first and second positions, a function based on the first position coordinates of the leaves; identifying a turning point for each function; and averaging the turning points. The function for each bank of leaves in each of the first and second positions is a second-order polynomial. Calculating of the distortion coefficient of the lens includes generating a function based on the first position coordinates and offsets of a selected one of the banks of leaves in one of the images; calculating a provisional distortion coefficient of the lens based on the function; determining an error value of the provisional distortion coefficient; if the error value is above a predetermined threshold, regenerating the function using the error value, recalculating the provisional distortion coefficient of the lens based on the regenerated function, and determining the error value of the recalculated provisional distortion coefficient until the error value is below the predetermined threshold; and when the error value is below the predetermined threshold, setting the distortion coefficient of the lens to be equal to the provisional distortion coefficient. The function is generated using a root mean square technique. Calculating the provisional distortion coefficient includes determining undistorted position coordinates, with respect to the predetermined coordinate space, for each leaf in the selected bank of leaves by minimizing, with the generated function, optical distortion associated with the lens; calculating a distortion coefficient of each leaf in the selected bank of leaves based on the undistorted position coordinates; and generating the provisional distortion coefficient of the lens by averaging the distortion coefficients of the leaves. The method additionally includes identifying the imaging marker positions of the leaves utilizing a predetermined conversion factor relating numbers of pixels and distance. Determining the offsets for the leaves includes identifying the imaging marker positions of the leaves, wherein each leaf is associated with at least two identified imaging marker positions; averaging, for each leaf, the imaging marker positions; identifying a reference leaf based on the average imaging marker positions; determining differences between the average imaging marker positions of the leaves and the average imaging marker position of the reference leaf; and calculating the offsets based on the determined differences.

According to another exemplary embodiment of the present disclosure, a computer-implemented method for use in a radiotherapy device that emits a radiation beam to treat a target tumour of a patient is provided. The radiotherapy device includes a multi-leaf collimator having a plurality of leaves, the leaves including imaging markers and configured to shape the radiation beam emitted by the radiotherapy device by blocking radiation. The radiotherapy device includes an imaging device configured to image the leaves. The imaging device includes a lens. The method includes receiving a treatment plan for treating the target tumour with radiation. The treatment plan includes a therapeutic radiation beam shape for irradiating the target tumour. The method includes identifying radiotherapy position coordinates, with respect to a predetermined coordinate space associated with the multi-leaf collimator, for the leaves of the multi-leaf collimator. The leaves form the therapeutic radiation beam shape by blocking radiation when they are positioned at the radiotherapy position coordinates. The method includes receiving offsets for the leaves. The offsets reflect differences between imaging marker positions of the leaves and positions of tips of the leaves. The method includes receiving calibration coefficients based on leaf position data from multiple multi-leaf collimators. The method includes generating a position error function based on the calibration coefficients. The position error function indicates a leaf position error associated with an optical distortion effect of the lens. The method includes controlling the leaves to move to the radiotherapy position coordinates based on the offsets and the position error function.

The multi-leaf collimator includes two opposing banks of leaves. Generating the position error function includes generating position error polynomials for the banks of leaves, wherein each position error polynomial is based on different calibration coefficients; receiving, from the imaging device, an image of the leaves; identifying distorted position coordinates, with respect to the predetermined coordinate space, for the leaves based upon positions of the imaging markers of the leaves in the image; and generating the position error function based on the position error polynomials and the distorted position coordinates of the leaves. Each bank of leaves is associated with three position error polynomials, and each position error polynomial is based on four calibration coefficients. The offsets of the leaves are determined, at least in part, from leaf position data obtained when the leaves are in a first position and upon leaf position data obtained when the leaves are in a second position. The position error function indicates a leaf position error of each leaf. The method additionally includes calculating corrected calibration coefficients to accommodate an adjustment of the multi-leaf collimator; and generating a corrected position error function based on the corrected calibration coefficients.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIG. 4A is a top plan view of two exemplary leaf banks with their tips aligned, consistent with various embodiments of the present disclosure.

FIG. 4B depicts a distorted image of the leaf banks of FIG. 4A captured by an exemplary leaf-imaging camera, consistent with various embodiments of the present disclosure.

FIG. 4C illustrates a barrel distortion effect caused by the lens of a leaf-imaging camera, consistent with various embodiments of the present disclosure.

DETAILED DESCRIPTION

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

Exemplary embodiments generally relate to systems and methods for minimizing or eliminating distortion in images of collimator leaves caused by the lens of a leaf-imaging camera. In addition, exemplary embodiments generally relate to systems and methods for accurately determining minor offsets of collimator leaves. Embodiments of the present disclosure may enable accurate determination of leaf positions, both during calibration and radiotherapy. Additionally, exemplary embodiments generally relate to systems and methods for performing radiotherapy, during which the positions of collimator leaves are corrected with generated position error functions.

Figure 1:
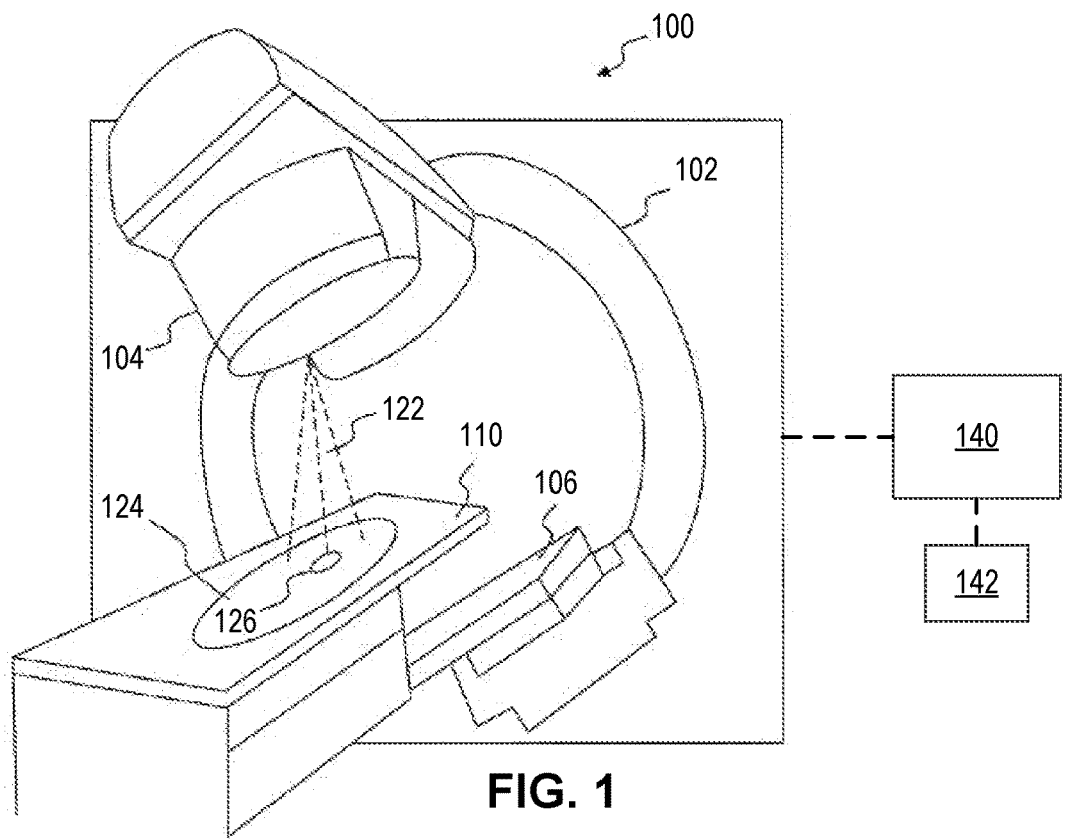
FIG. 1 illustrates an exemplary radiotherapy system, consistent with various embodiments of the present disclosure.

FIG. 1 is a view of an exemplary radiotherapy system 100. System 100 may be a linear accelerator (LINAC) system or a combination magnetic resonance imaging (MRI) and linear accelerator system, known as an MR-LINAC. However, it will be appreciated that system 100 in the present disclosure is not limited to a LINAC or a MR-LINAC, and that the systems and devices disclosed herein may be used to enable any suitable radiotherapy system, or any suitable combination medical imaging and radiotherapy system.

System 100 may include a chassis 102, which may support a radiation head 104 and a radiation detection panel 106. Radiation head 104 and detection panel 106 may be mounted opposite each other on chassis 102, with a rotational axis of chassis 102 positioned between them. Radiation head 104 may be configured to generate a radiation beam 122, such as according to a treatment plan, to deliver doses of radiation to a patient 124 supported by a couch 110. The treatment plan may be predetermined, or may be determined in real-time or just prior to treatment and may be adjusted during the course of treatment. Chassis 102 may be configured to rotate radiation head 104 and detection panel 106 about couch 110, to provide patient 124 with a plurality of varying dosages of radiation according to the treatment plan. For example, chassis 102 may be powered by one or more chassis motors such that chassis 102 is continuously rotatable around couch 110. In some embodiments, couch 110 may be motorized so that the patient 124 can be positioned with a tumour site at or close to the isocentre 126 of the radiation beam 122. Additionally or alternatively, simultaneously with rotation of chassis 102 about the patient 124, couch 110 may be moved along a translation axis into or out of the treatment area (i.e. parallel to the axis of rotation of the chassis). With this simultaneous motion, a helical radiation delivery pattern known in the art may be achieved for producing certain types of dose distributions.

In some embodiments, system 100 may additionally include an imaging device. For example, system 100 may be configured as an MR-LINAC system. Exemplary system 100 may utilize MR images, CT images, and/or pseudo-CT images to monitor and control radiation delivered by radiation head 104.

System 100 may additionally include a controller 140, which may be programmed to control, inter alia, radiation head 104, detection panel 106, couch 110, an imaging device, and the chassis motor. Controller 140 may perform functions or operations such as treatment planning, treatment execution, image acquisition, image processing, motion tracking, motion management, and/or other tasks involved in a radiotherapy process. Hardware components of controller 140 may include one or more computers (e.g., general purpose computers, workstations, servers, terminals, portable/mobile devices, etc.); processors (e.g., central processing units (CPUs), graphics processing units (GPUs), microprocessors, digital signal processors (DSPs), field programmable gate arrays (FPGAs), special-purpose or specially-designed processors, etc.); memory/storage devices such as a memory 142 (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); circuitries; printed circuit boards (PCBs); or other suitable hardware. Software components of controller 140 may include operation system software, application software, etc.

Controller 140 may be programmed to control features of system 100 according to a radiotherapy treatment plan for irradiating a target tissue of a patient. The treatment plan may include information about a particular dose to be applied to a target tissue, as well as other parameters such as beam angles, dose-histogram-volume information, the number of radiation beams to be used during therapy, the dose per beam, and the like. Controller 140 may be programmed to control various components of system 100, such as chassis 102, radiation head 104, detection panel 106, and couch 110, according to the predetermined treatment plan. In some embodiments, controller 140 may be programmed to generate a treatment plan using images received from an imaging device. Alternatively or additionally, controller 140 may be programmed to acquire a treatment plan from memory 142 and to execute the plan with system 100. In some embodiments, controller 140 may be programmed to modify a treatment plan received from memory 142 prior to execution with system 100.

Figure 2:
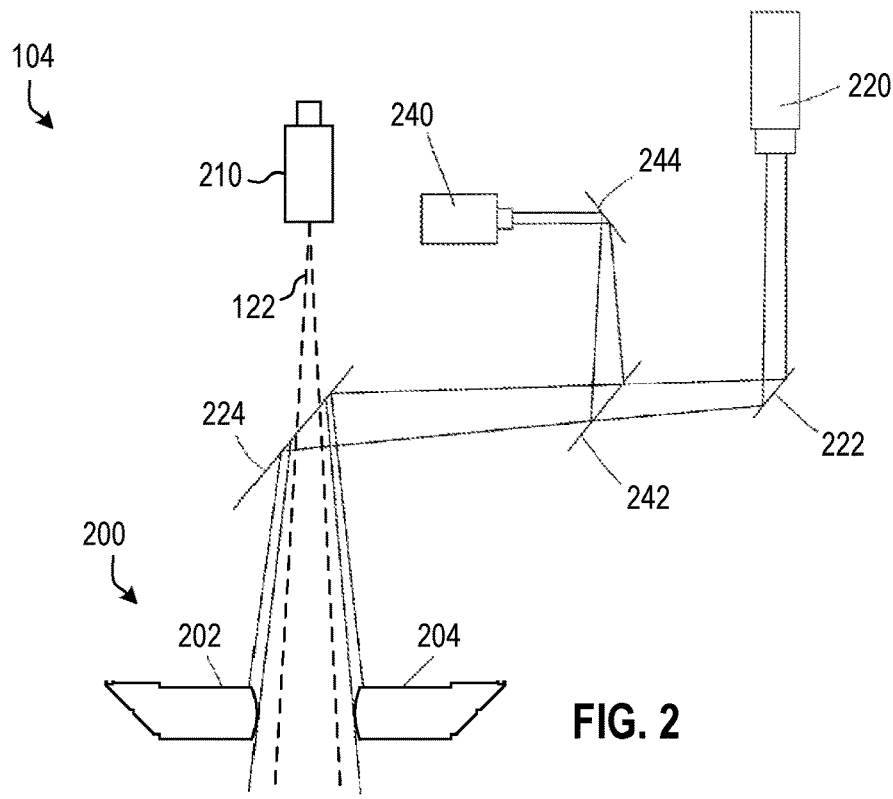
FIG. 2 illustrates an exemplary radiation head of the radiotherapy system of FIG. 1, consistent with various embodiments of the present disclosure.

FIG. 2 illustrates features of an exemplary radiation head 104 of system 100. Radiation head 104 may include a radiation beam generator 210 (e.g. an X-ray source) and a multi-leaf collimator (MLC) 200, at least one of which may be mounted on chassis 102. Radiation beam 122, generated by beam generator 210, may be a cone beam or a fan beam, for example. In other embodiments, radiation head 104 may include more than one beam generator and/or more than one respective multi-leaf collimator. MLC 200 may include a plurality of elongate leaves 202, 204 oriented orthogonal to the axis of beam 122. The leaves of MLC 200 may be controlled to take different positions to selectively block some or all of radiation beam 122, thereby altering the shape of the beam that reaches the patient.

Radiation head 104 may also include a camera 220 configured to view collimator leaves 202, 204 via a pair of tilt-adjustable mirrors 222, 224, which may permit the camera to be located out of the radiation beam 122. In some embodiments, leaves 202, 204 may not be visible to camera 220; accordingly, leaves 202, 204 may include imaging markers mounted thereon, such as rubies or fluorescing markers, which may be visible to camera 220. A beam splitter 242 may be placed in the optical path (between the two mirrors 222, 224) so that it is also out of the radiation beam 122) such that a light projector 240 may illuminate the imaging markers along the same optical path. Radiation head 104 may include a further mirror or mirrors 244 so as to locate the light projector (and/or other elements) in convenient locations.

According to embodiments in which leaves 202, 204 each include a ruby as an imaging marker, the ruby may be configured to fluoresce in the dark red/near infrared light band (e.g. 695 nm) when illuminated with light having a wavelength in the 525 nm green light band or in the 410 nm violet/near ultraviolet light band. For example, light projector 240 may irradiate the rubies with green or violet light such that the rubies fluoresce, emitting light which may be diverted to camera 220 by mirrors 222, 224. Camera 220 may generate image data of the leaves 202, 204 utilizing the light emitted by the rubies, and controller 140 may utilize the image data to determine the position of the leaves and to control movement of the leaves into or out of the path of radiation beam 122 so as to shape the beam (e.g. according to a predetermined treatment plan). It will be appreciated that radiation head 104 in the present disclosure is not limited to the leaf-imaging configuration depicted in FIG. 2, and that the systems and devices disclosed herein may include any suitable configuration to image the leaves of MLC 200.

Figure 3A:
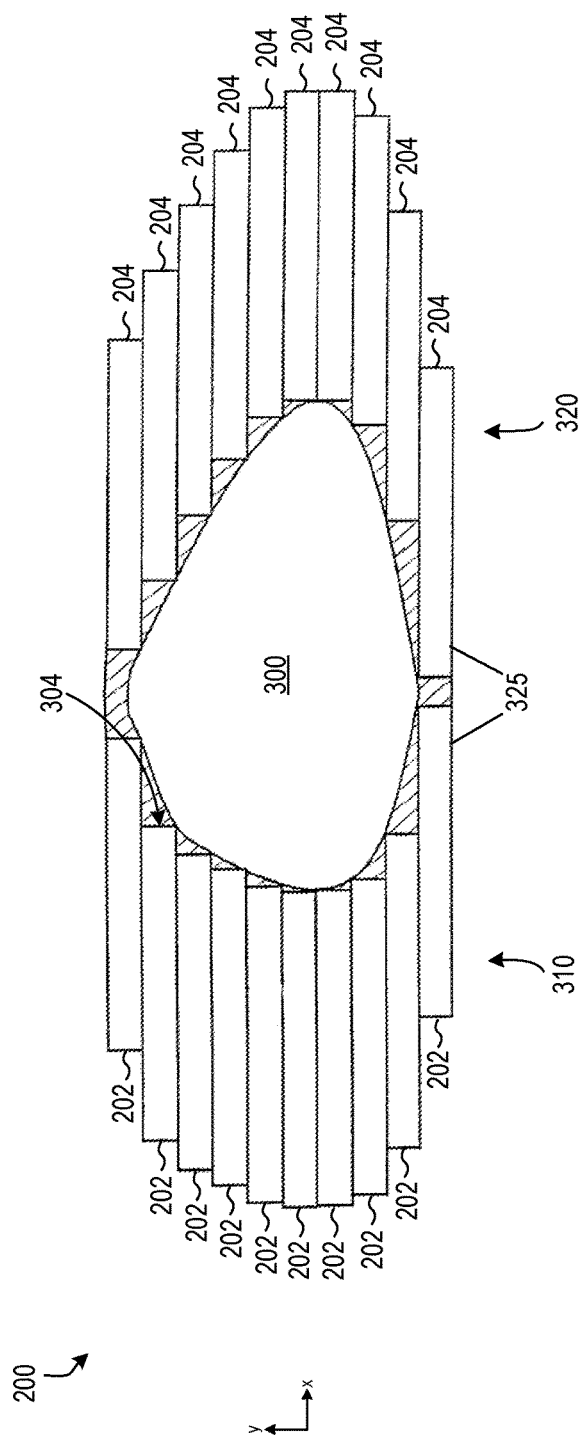
FIG. 3A is a top plan view of an exemplary leaf array of a multi-leaf collimator, consistent with various embodiments of the present disclosure.
Figure 3B:
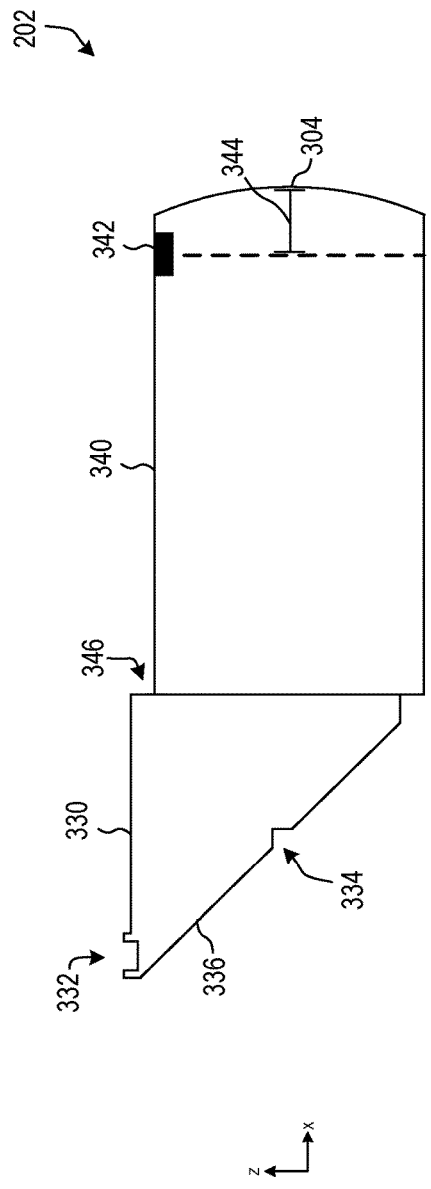
FIG. 3B is a side view of an exemplary leaf of a multi-leaf collimator, consistent with various embodiments of the present disclosure.

FIG. 3A is a top plan view of an exemplary leaf array of MLC 200, and FIG. 3B is a side view of an exemplary leaf 202. MLC 200 may include two banks 310, 320 of leaves, each of which may be individually extended into and out of the path of radiation beam 122 so that their respective tips 304 shape the cross-section of the beam by blocking portions thereof. The word "tip" may refer to a functional end of leaf 202 along a longitudinal axis thereof for purposes of forming a shaping window for radiation beam 122. The word "tip" does not necessarily refer to the end point of leaf 202 relative to the longitudinal axis thereof (that is, the point of the leaf 202 closest to the center of MLC 200), although in some embodiments it may refer to the end point of leaf 202 relative to the longitudinal axis thereof. In some embodiments, MLC 200 may include a bank of motors, each configured to move a corresponding one of the leaves. Movement of each leaf by the motors may be controlled by controller 140; for example, controller 140 may control placement of the leaf tips 304 via the motors to shape radiation beam 122 for irradiating a target tissue 300, such as according to a predetermined treatment plan. In some embodiments, leaves 202, 204 may be configured to be extended into the path of radiation beam 122 to a location beyond a halfway point between leaf banks 310, 320. This capability may allow the leaves 202, 204 to be fully closed together. Leaves 202, 204 may be constructed of a radiopaque material such as tungsten and may be arranged side-by-side relative to each other, in two opposing banks 310, 320; thus, areas beneath the leaves 202, 204 are not irradiated. Each leaf is positioned directly opposite a corresponding leaf in the other leaf bank; two opposing leaves constitute a leaf pair 325. Each leaf may be thin in its transverse (y) direction to provide high resolution and limit the size of unnecessarily irradiated tissue areas. Each leaf may also be deep in the (z) direction to provide effective radiation absorption. In some embodiments, each bank may include 80 leaves, resulting in 160 leaves in total; alternatively, MLC 200 may include more or fewer leaves.

Each leaf 202, 204 may include a drive coupling 330 and a tungsten body 340 secured together. The drive coupling 330 may include two grooves 334, 346 configured to engage end stop bars which may limit movement of the leaf (discussed further below). The drive coupling 330 may additionally include a notch 332 near the rear end 336 thereof, the notch 332 being configured to engage the leaf motor. For example, the leaf motor may be connected to a leaf key which may be inserted into notch 332 and driven by the motor to move the leaf into and out of radiation beam 122. Tungsten body 340 may include an imaging marker 342 (e.g. a ruby) positioned near the leaf tip 304. The imaging marker 342 of each leaf is manually placed approximately a predetermined distance from leaf tip 304. For example, imaging marker 342 may be placed such that its centre is approximately 4.5 millimeters from leaf tip 304. However, because each imaging marker is manually placed, the minor offset 344 between the centre of imaging marker 342 and the leaf tip 304 may be different for each leaf. Camera 220 cannot measure minor offset 344 by imaging the position of the leaf tip 304 because leaf 202 is not visible to the camera 220 except for imaging marker 342.

FIG. 4A is a top plan view of leaf banks 310 and 320, with their tips 304 aligned in two straight lines. For example, each leaf depicted in FIG. 4A may be in a respective fully retracted position. FIG. 4B is an image of imaging markers 342, as captured by camera 220. In the configuration depicted in FIG. 4A, imaging markers 342 of the leaves are approximately aligned on two straight lines because the markers are roughly the same distance from the aligned tips. As depicted in FIG. 4B, camera 220 captures an image of markers 342. However, the lens of camera 220 distorts the image of markers 342: markers 342 appear, in the image, to form two curved lines, rather than two approximately straight lines. This distortion effect, which is known as "barrel distortion" and which is illustrated in FIG. 4C, compresses image features to appear closer to the centre 400 of the image the further they are from the x coordinate axis 402 and y coordinate axis 404 of the image. Thus, as depicted in FIG. 4C, straight lines 406 are distorted to appear as curved lines 408, with the curve becoming more pronounced the further the line extends away from the x-axis 402 and y-axis 404 of the image. The barrel distortion effects are different for each camera lens and can make it difficult to determine the true positions of the collimator leaves, especially for the leaves furthest from the centre of the collimator. Therefore, in order to accurately locate and position the collimator leaves, the barrel distortion must be quantified and removed.

Figure 5A:
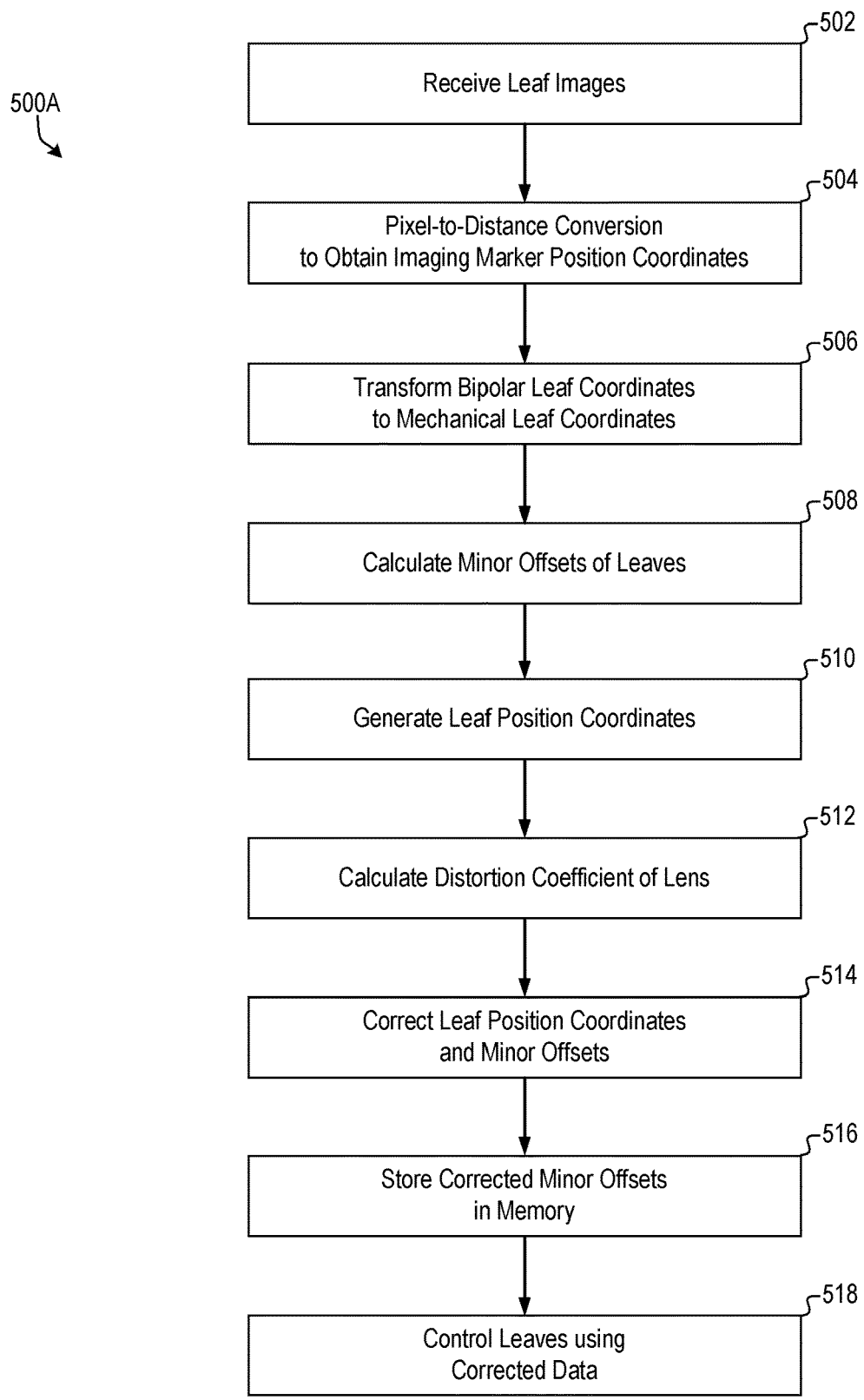
FIG. 5A is a flow diagram of an exemplary calibration method for a multi-leaf collimator, consistent with various embodiments of the present disclosure.

FIG. 5A illustrates an exemplary calibration method 500A for a multi-leaf collimator (e.g. MLC 200) in which the barrel distortion and minor offsets may be quantified and used to correct the detected positions of the collimator leaves. Method 500A may be a processor-executed method. In some embodiments, method 500A may be executed by the same processor, such as controller 140. Alternatively, one or more steps of method 500A can be executed by separate processors.

In step 502, controller 140 may control movement of the collimator leaves and may receive images of the leaves from camera 220. The controller may identify position data of the imaging markers 342 from the received images. Step 502 may include receiving two or more images of the leaves from camera 220. Controller 140 may be programmed to control MLC 200 such that each bank of leaves 310, 320 may be in a different position in each of the images. Optionally, controller 140 may store the position data of the imaging markers in memory 142.

Figure 6A:
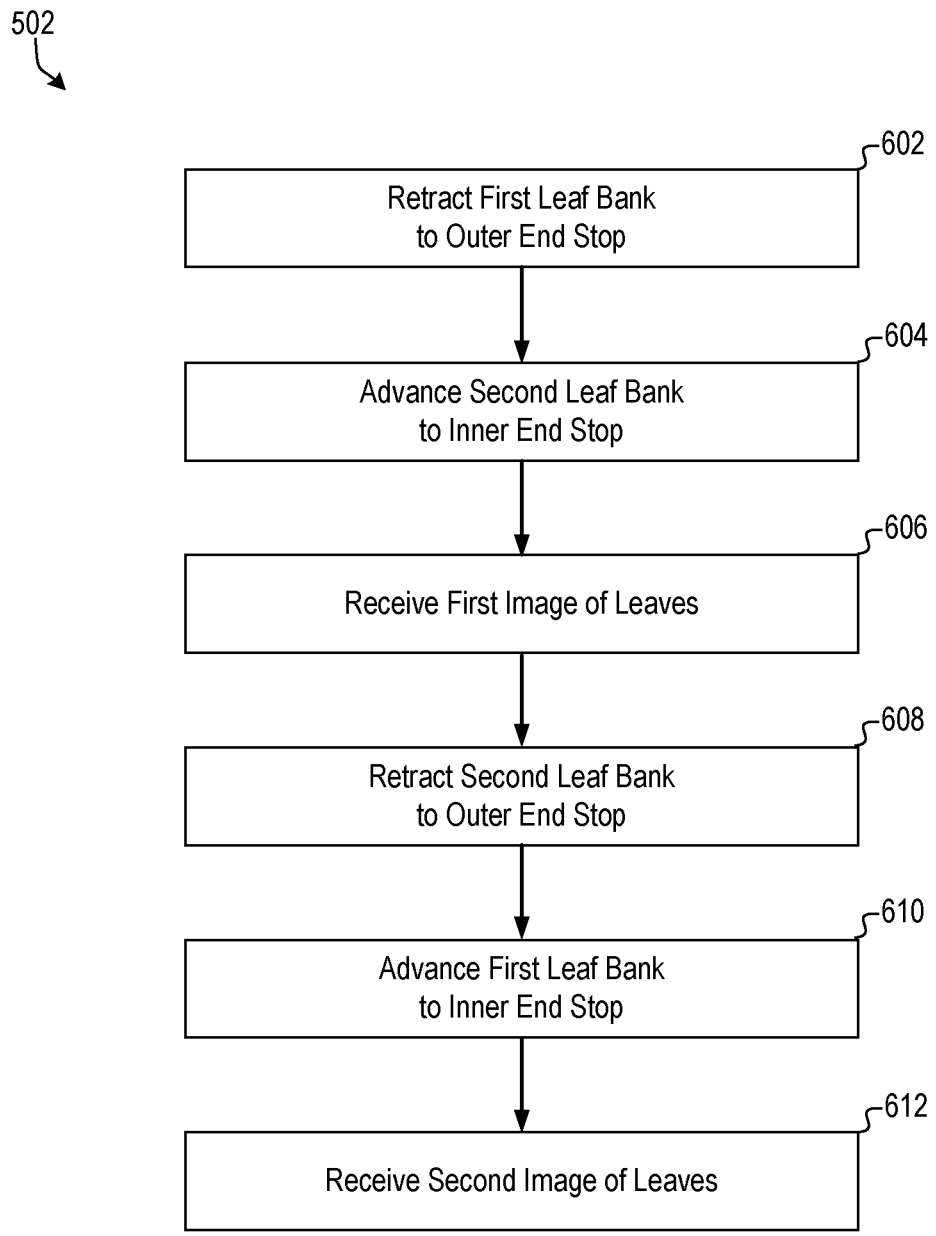
FIG. 6A is a flow diagram of an exemplary leaf imaging method, consistent with various embodiments of the present disclosure.

FIG. 6A illustrates an exemplary process of step 502. The process of FIG. 6A may be executed by a processor, such as controller 140. In step 602, controller 140 may retract a first bank of leaves (e.g. leaf bank 310) to an outer end stop 622. In step 604, controller 140 may advance the other bank of leaves (e.g. leaf bank 320) to an inner end stop 624. In some embodiments, leaves in the advancing bank (e.g. leaf bank 320) may be advanced beyond the halfway point between the leaf banks 310, 320 when they are advanced to the inner end stop 624. Controller 140 may move the leaves, including advancing and retracting the leaves to the end stops, by actuation of the leaf motors of system 100.

Figure 6B:
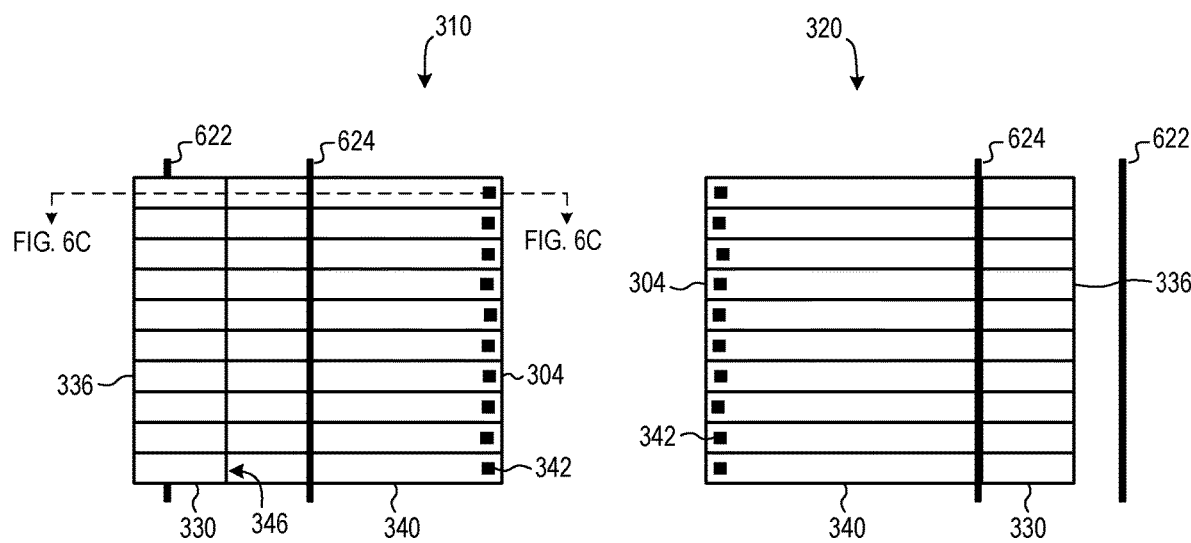
FIG. 6B is a top plan view of two exemplary banks of leaves in a first configuration during the leaf imaging method of FIG. 6A, consistent with various embodiments of the present disclosure.
Figure 6C:
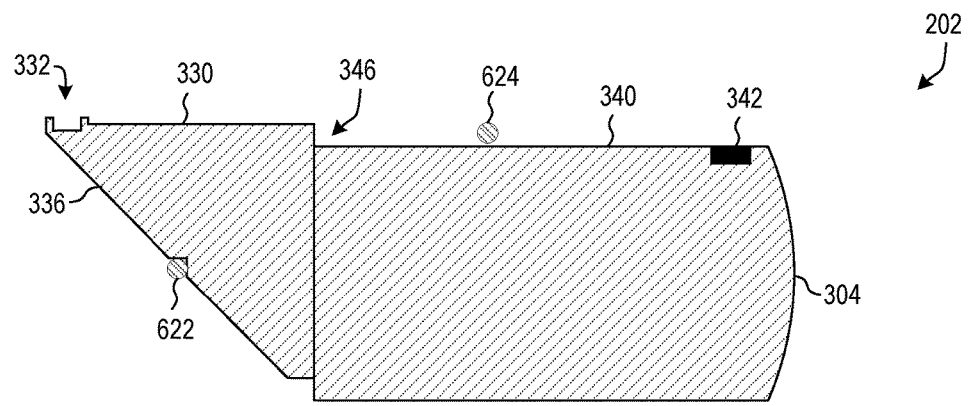
FIG. 6C is a cross-sectional side view of an exemplary leaf in the first configuration of FIG. 6B, consistent with various embodiments of the present disclosure.

FIGS. 6B and 6C illustrate a first exemplary configuration of retracted and extended leaves. Each leaf bank 310, 320 may include an outer end stop 622 and an inner end stop 624. The end stops 622, 624 may be situated perpendicular to the longitudinal axis of the leaves and may limit movement of the leaves. For example, outer end stop 622 may engage groove 334 on the rear end 336 of drive coupling 330, and may define the fully retracted position of the leaves because the leaves cannot be retracted away from the collimator centre beyond outer end stop 622. Inner end stop 624 may engage groove 346 and may define the fully extended position of the leaves because the leaves cannot be advanced towards the collimator centre past inner end stop 624. However, one of ordinary skill will appreciate that the configurations of leaves 202, 204 and of end stops 622, 624 are merely exemplary, and that the systems and devices disclosed herein may include any suitable configuration to define fully retracted and fully extended positions of the collimator leaves.

In step 602 (FIG. 6A), controller 140 may retract leaf bank 310 away from the collimator centre until grooves 334 of the drive couplings 330 engage outer end stop 622, as illustrated in the cross-sectional view of FIG. 6C. In step 604, controller 140 may advance leaf bank 320 towards the collimator centre until grooves 346 of the leaves in the bank engage inner end stop 624. In this arrangement, leaf tips 304 and rear ends 336 of the leaves in each bank may be aligned in straight lines because the leaves are identically shaped and dimensioned (with the exception of the manual placement of imaging marker 342). In step 606, controller 140 may control camera 220 to capture a first image of the leaves and may receive the image from camera 220. In some embodiments, controller 140 may store the first image in memory 142.

Figure 6D:
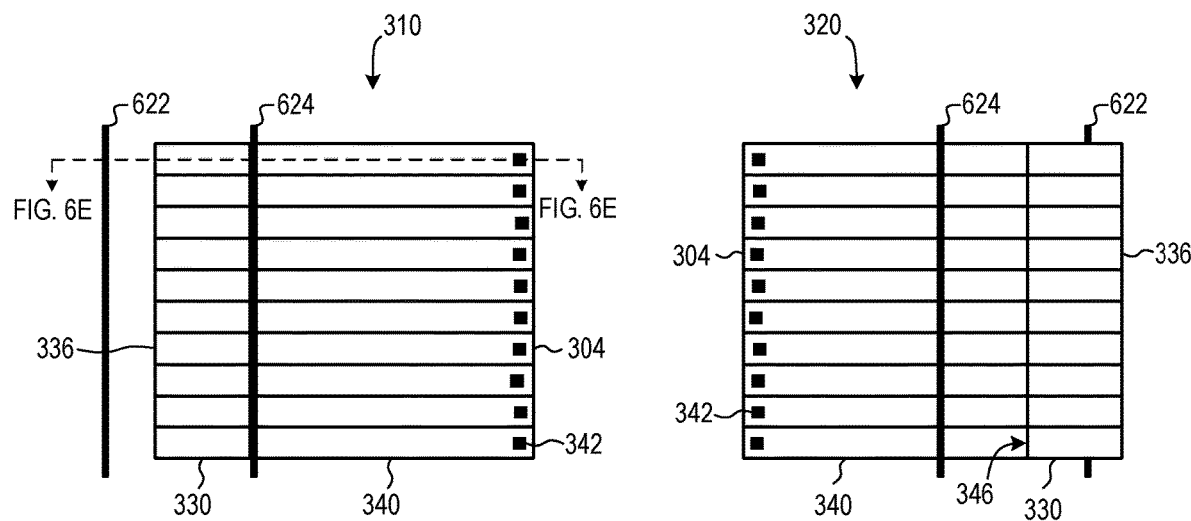
FIG. 6D is a top plan view of two exemplary banks of leaves in a second configuration during the leaf imaging method of FIG. 6A, consistent with various embodiments of the present disclosure.
Figure 6E:
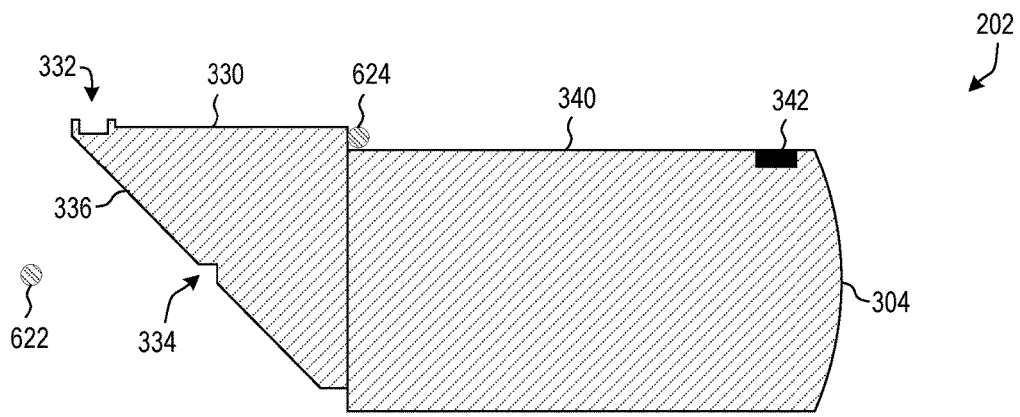
FIG. 6E is a cross-sectional side view of an exemplary leaf in the second configuration of FIG. 6D, consistent with various embodiments of the present disclosure.

FIGS. 6D and 6E illustrate steps 608-612. In step 608, controller 140 may advance bank 310 until grooves 346 of the leaves in the bank engage inner end stop 624, as illustrated in the cross-sectional view of FIG. 6E. In some embodiments, leaves in the advancing bank (e.g. leaf bank 310) may be advanced beyond the halfway point between the leaf banks 310, 320 when they are advanced to inner end stop 624. In step 610, controller 140 may retract leaf bank 320 away from the collimator centre until grooves 334 of leaves in the bank engage outer end stop 622. In step 612, controller 140 may control the camera 220 to capture a second image of the leaves and may receive the image from camera 220. In some embodiments, controller 140 may store the second image in memory 142.

One of ordinary skill will understand that controller 140 may execute steps 608-612 prior to executing steps 602-606. In addition, controller 140 may control camera 220 to capture more than two images of the leaves. For example, controller 140 may image banks 310 and 320 separately in their respective fully extended and fully retracted configurations, resulting in four total images. However, at a minimum, two images of the leaves must be collected because the leaves must be imaged in at least two different positions.

Referring again to FIG. 5A, in step 504, controller 140 may identify the positions of imaging markers 342 within the images received in steps 606 and 612. Controller 140 may identify the positions of the imaging markers in both banks of leaves in the retracted and advanced positions. Thus, for a given leaf of MLC 200, controller 140 may identify the imaging marker position from the image of that leaf in the advanced position and may identify the imaging marker position from the image of that leaf in the retracted position. Controller 140 may convert the imaging marker position data from pixels to a unit of distance, such as millimeters or microns, using a predetermined conversion factor. In some embodiments, the conversion factor may be constant for all leaves of MLC 200. The conversion factor may be calculated from a measured distance of a leaf travel trajectory in millimetres (which may be determined based upon the known dimensions of MLC 200) and a measured distance of the same leaf travel trajectory in pixels (which may be captured by camera 220 and corrected in accordance with, for example, method 500A). Additionally or alternatively, a conversion factor may be estimated from a number of MLCs and averaged or otherwise combined to produce the conversion factor. In step 504, controller 140 may determine x and y position coordinates for the imaging markers, with respect to a predetermined coordinate space 520 associated with MLC 200, based upon the converted imaging marker position data. Each leaf of MLC 200 may be associated with two sets of imaging marker position coordinates: one set of imaging marker position coordinates representing when the leaf is fully advanced and another set of imaging marker position coordinates representing when the leaf is fully retracted. In some embodiments, controller 140 may store the imaging marker position coordinates in memory 142. In some embodiments, controller 140 may perform the pixel-to-distance conversion of step 504 prior to determining the imaging marker position coordinates. In alternative embodiments, controller 140 may determine the imaging marker position coordinates in pixels, and may perform steps 506-514 of method 500A, and optionally step 516 of method 500A, using measurements and calculations in pixels. In such embodiments, controller 140 may then perform the pixel-to-distance conversion prior to performing the leaf control of step 518.

In some embodiments, controller 140 may receive multiple images of the leaves at step 606 and at step 612. For example, controller 140 may receive 2 images, 3 images, 4 images, 5 images, 10 images, 25 images, 50 images, 100 images, or some other number of images at step 606 and at step 612. Controller 140 may execute step 504 of method 500A for each image received in steps 606 and 612 and may thus calculate imaging marker position coordinates for imaging marker 342 in each received image. In some embodiments, the imaging marker position coordinates from each image of a given leaf at a given position (e.g., from each image of the first leaf of left bank 310 in the retracted position) may be averaged to generate a more accurate set of position coordinates for the imaging marker of each leaf at each position. The average imaging marker position coordinates may be utilized by controller 140 in executing the remainder of method 500A.

Figure 5B:
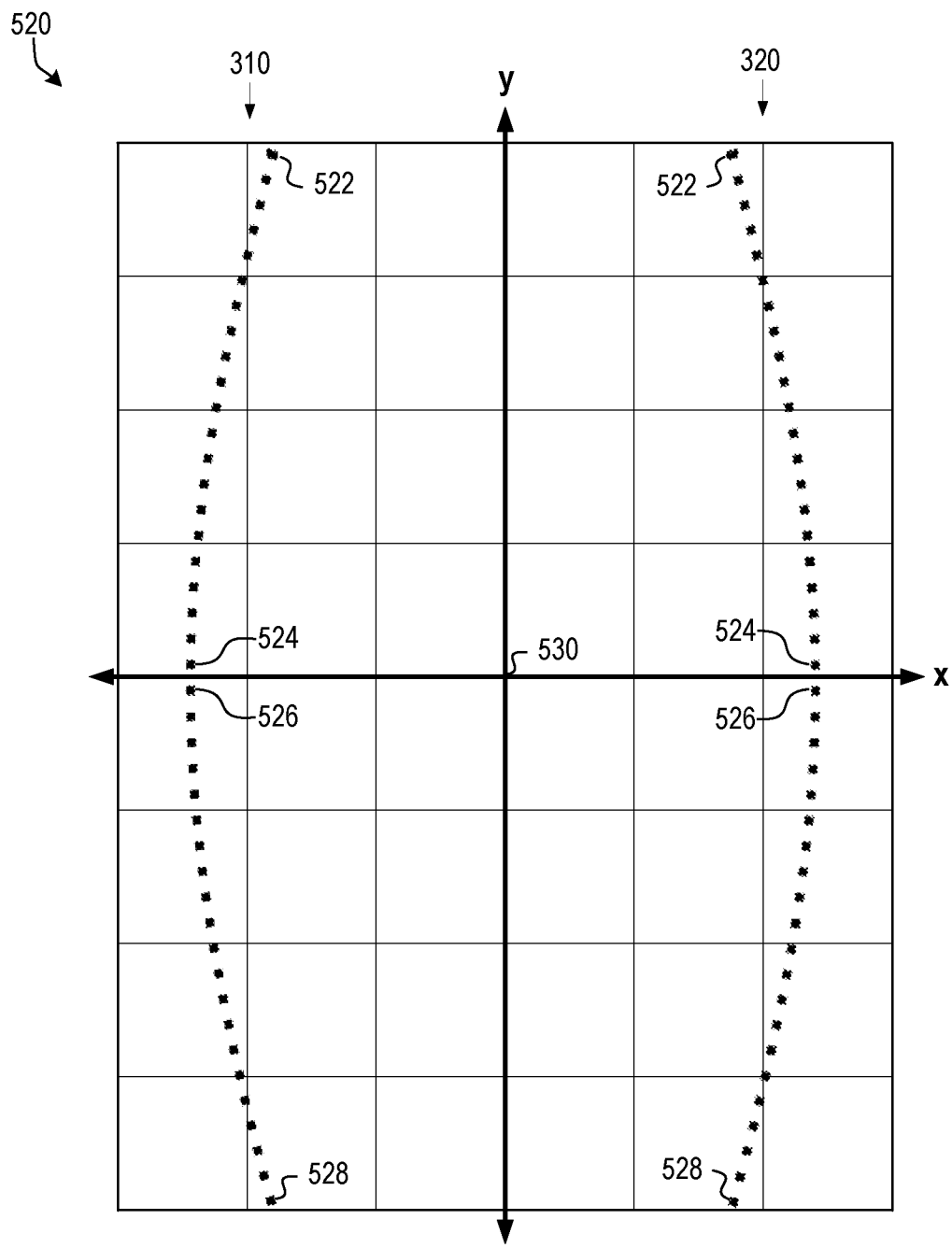
FIG. 5B depicts a predetermined coordinate space associated with the multi-leaf collimator, consistent with various embodiments of the present disclosure.

FIG. 5B depicts an exemplary predetermined coordinate space 520 associated with MLC 200, with the position coordinates for each imaging marker 342 mapped therein. The position coordinates of the imaging markers may be affected by the barrel distortion of the camera lens. For example, in a MLC with 80 leaves per leaf bank, markers of the first leaf 522 and $80^{th}$ leaf 528 may appear closer to the y-axis than markers of the $40^{th}$ leaf 524 and $41^{st}$ leaf 526, though in reality the markers may be placed in approximately straight lines. The imaging marker position coordinates for a first bank of leaves (e.g. leaf bank 310) may have negative x-coordinates (i.e. are positioned to the left of the y-axis), while the imaging marker position coordinates for a second bank of leaves (e.g. leaf bank 320) may have positive x-coordinates (i.e. are positioned to the right of the y-axis). In some embodiments, controller 140 may determine imaging marker position coordinates with the origin 530 of the coordinate space 520 corresponding to the position of the collimator centre. In a MLC with 80 leaves per leaf bank (160 leaves total), the collimator centre may be located between the $40^{th}$ leaf 524 and the $41^{st}$ leaf 526, relative to an axis perpendicular to longitudinal directions of the leaves, and may be located equidistantly between the two leaf banks 310, 320. In some alternative embodiments, controller 140 may position origin 530 at a point which is equidistant between leaf banks 310, 320 and above first leaf 522 (relative to FIG. 5B) or below $80^{th}$ leaf 528 (relative to FIG. 5B). Thus, the imaging marker position coordinates in coordinate space 520 may be assigned relative to the collimator centre.

Returning to method 500A in FIG. 5A, controller 140 may transform the imaging marker position coordinates from the bipolar coordinate system to a mechanical coordinate system in step 506, so as to correct the x-coordinates of markers measured relative to the negative portion of x-axis 402 (i.e. markers in leaf bank 310). Controller 140 may execute this transformation by multiplying the x-coordinates of the imaging markers in leaf bank 310 by −1. In some alternative embodiments, controller 140 may execute the bipolar-to-mechanical transformation at a different step of method 500A, such as at the beginning of step 512.

Figure 7:
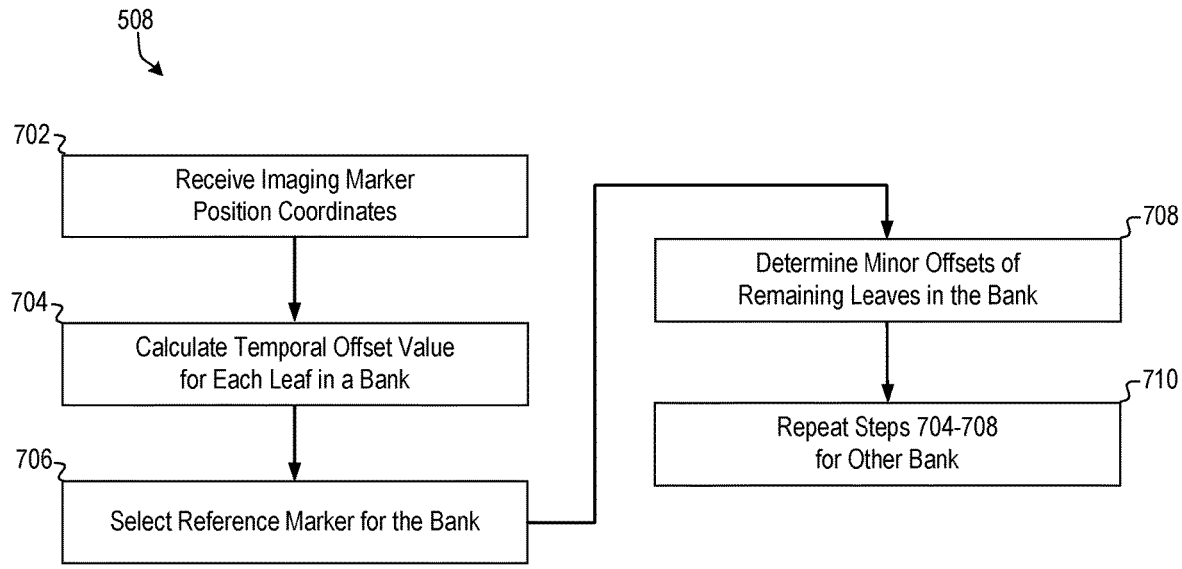
FIG. 7 illustrates an exemplary method of calculating minor offsets of collimator leaves, consistent with various embodiments of the present disclosure.

Controller 140 may calculate minor offset values for leaves in step 508. FIG. 7 illustrates an exemplary process of calculating the minor offsets in step 508. The leaves of MLC 200 may be identically shaped and dimensioned; for example, the leaf length 720, length 722 of drive coupling 330, and length 724 of body 340 may be constant for all leaves of MLC 200. However, because each marker 342 is manually and individually placed, minor offset 344 may vary across the leaves.

At step 702, controller 140 may obtain the imaging marker position coordinates determined in step 504. The obtained imaging marker position coordinates may include the imaging marker position coordinates for the imaging marker of each leaf at each position (that is, in the advanced position and in the retracted position). In step 704, for one bank of leaves, controller 140 may calculate a temporal offset valve $offset_{temp}$ for the imaging marker of each leaf. Controller 140 may calculate $offset_{temp}$ for a given marker according to the following:

$$offset_{temp} = \frac{|x_{outer} - x_{inner}|}{2}$$

where $x_{outer}$ represents the x-coordinate of the marker when the leaf is at the fully retracted position and $x_{inner}$ represents the x-coordinate of the marker when the leaf is at the fully advanced position. Thus, $offset_{temp}$ may be considered an average x-coordinate for the marker of a given leaf. Offset$_{temp}$ has a positive value. In step 706, controller 140 may identify a reference marker from among the imaging markers 342 in the bank. In some embodiments, the reference marker may be the imaging marker with the largest offset$_{temp}$ value (that is, the imaging marker with the x-coordinate which is furthest from the y-axis of coordinate space 520). In some alternative embodiments, the reference marker may be the imaging marker with the smallest offset$_{temp}$ value (that is, the imaging marker with the x-coordinate which is closest to the y-axis of coordinate space 520).

In step 708, controller 140 may calculate the minor offsets 344 for the remaining leaves in the bank. In some embodiments, the reference marker may be assumed to have a predetermined minor offset. For example, the leaves of MLC 200 may be manufactured such that each marker 342 is placed approximately a predetermined distance (e.g. 4.5 millimeters) from the leaf tip 304. Controller 140 may assume that the reference marker has a minor offset 344 equal to this distance (e.g. 4.5 millimeters) and may utilize the offset$_{temp}$ values of the reference leaf and of the remaining leaves in the bank to calculate the minor offsets 344 of the other leaves. In some embodiments, controller 140 may determine longitudinal distances (i.e. distances along the x-axis of coordinate space 520) between offset$_{temp}$ of the reference marker and the offset$_{temp}$ values of the other markers in the bank. Controller 140 may then subtract the determined longitudinal distances from the predetermined distance to calculate the minor offsets of the leaves. According to an example in which the predetermined distance is 4.5 millimetres, if the controller determines that the offset$_{temp}$ of a given marker is 0.3 millimeters from the offset$_{temp}$ of the reference marker, controller 140 may determine that the given marker has a minor offset of 4.2 millimeters (i.e. 4.5 mm-0.3 mm). The controller may perform this calculation for all leaves in the bank. In step 710, controller 140 may calculate the minor offsets for the leaves in the other bank according to steps 704-708.

As mentioned above, in some alternative embodiments of step 706 the marker closest to the collimator centre may be selected by controller 140 as the reference marker. In such embodiments, controller 140 may assume that the reference marker has a minor offset equal to the predetermined distance (e.g. 4.5 millimeters) and may add the determined longitudinal distances between the reference marker and the remaining markers to the predetermined distance to calculate the minor offsets of the leaves in step 708. For example, if it is determined that offset$_{temp}$ of a given marker is 0.1 millimeter from offset$_{temp}$ of the reference marker, controller 140 may determine that the given marker has a minor offset of 4.6 millimeters (i.e. 4.5 mm+0.1 mm). Controller 140 may perform this calculation for all remaining leaves in the bank. In step 710, controller 140 may calculate the minor offsets for the leaves in the other bank Advantageously, controller 140 may identify the imaging marker with the largest temporal offset value (that is, the marker which is furthest from the collimator centre) as the reference marker in some embodiments because the leaf of that marker is likely to be in the fully retracted configuration. Because the leaves themselves are not visible to camera 220, it cannot be confirmed with camera 220 that all of the leaves are actually in contact with outer end stop 622 when in the fully retracted position. It is highly likely that the leaf with the imaging marker furthest from the collimator centre is in the fully retracted position, since the imaging marker is drawn away from the collimator centre when the leaf is retracted towards outer end stop 622. Therefore, the determined minor offset of the reference marker is highly likely to be accurate, allowing calculation of the other minor offset values to be accurate as well.

Returning to method 500A of FIG. 5A, in step 510 controller 140 may calculate leaf position coordinates corresponding to the position of tips 304 of the collimator leaves relative to coordinate space 520. The leaf position coordinates may include an x-coordinate and a y-coordinate of each leaf tip 304. For a given leaf at a given position (that is, either the advanced position or the retracted position), the value of the minor offset may be subtracted from the value of the imaging marker x-coordinate to determine the value of the leaf position x-coordinate. In this way, the minor offset may be corrected for and the x-coordinate of the leaf tip identified. For a given leaf at a given position, the value of the leaf position y-coordinate may be equal to the value of the imaging marker y-coordinate. Because minor offset only distorts calculation of the leaf position along the x-axis, the y-coordinates of the leaves do not require correction for the minor offset. Controller 140 may calculate leaf position coordinates for each leaf in the advanced position and in the retracted position. That is, each leaf of MLC 200 may be associated with two sets of leaf position coordinates: one set of coordinates representing when the leaf is fully advanced and another set of coordinates representing when the leaf is fully retracted.

Figure 8:
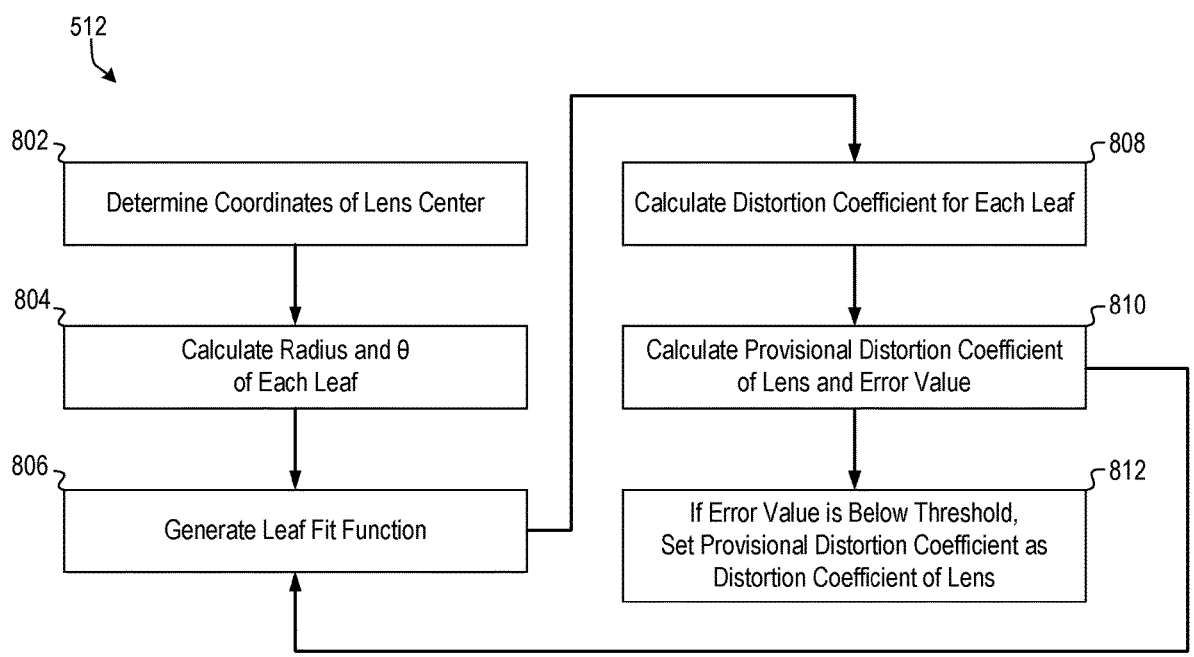
FIG. 8 is a flow diagram of an exemplary method of calculating a distortion coefficient of an imaging lens, consistent with various embodiments of the present disclosure.

Once the leaf position coordinates are determined, a distortion coefficient which quantifies the barrel distortion effect associated with the camera lens may be determined in step 512. FIG. 8 illustrates an exemplary process of calculating a distortion coefficient k in step 512. Distortion coefficient k characterizes the barrel distortion behavior of the lens and is different for each lens. Distortion coefficient k can be approximated to a third degree Taylor series and expressed by the following formula:

$$r_{distorted} = r_{undistorted} \cdot (1 + k \cdot r_{undistorted}^2)$$

where $r_{distorted}$ is the radius of a point from the lens centre for a distorted image, and $r_{undistorted}$ is the radius of a point from the lens centre for an undistorted image. Since barrel distortion compresses an image, $r_{distorted}$ is smaller than $r_{undistorted}$. Since both radii are, by definition, positive:

$$r_{distorted} < r_{undistorted} \Rightarrow \frac{r_{distorted}}{r_{undistorted}} < 1 \Rightarrow$$
$$\Rightarrow 1 + k \cdot r_{undistorted}^2 < 1 \Rightarrow k \cdot r_{undistorted}^2 < 0 \Rightarrow k < 0$$

Thus, distortion coefficient k must be less than 0. By determining distortion coefficient k of the lens, the barrel distortion can be quantified and removed. Calculation of distortion coefficient k may be performed with the imaging marker positions represented in pixels or in a unit of distance (e.g. microns); however, all calculations must be made in the same units.

Prior to executing step 802 depicted in FIG. 8, controller 140 may perform the bipolar-to-mechanical transformation, if the transformation was not performed earlier in method 500A. In step 802, controller 140 may determine x- and y-position coordinates of the lens centre within to coordinate space 520. The lens centre represents the origin of the distortion introduced by the lens of camera 220; that is, the lens centre is the point of the lens through which light passing through the lens is undistorted. In some cases, the lens centre may be at origin 530; in other cases, it may be at a different location in coordinate space 520. Either the x-coordinate or the y-coordinate of the lens centre may be calculated first by controller 140.

Figure 9B:
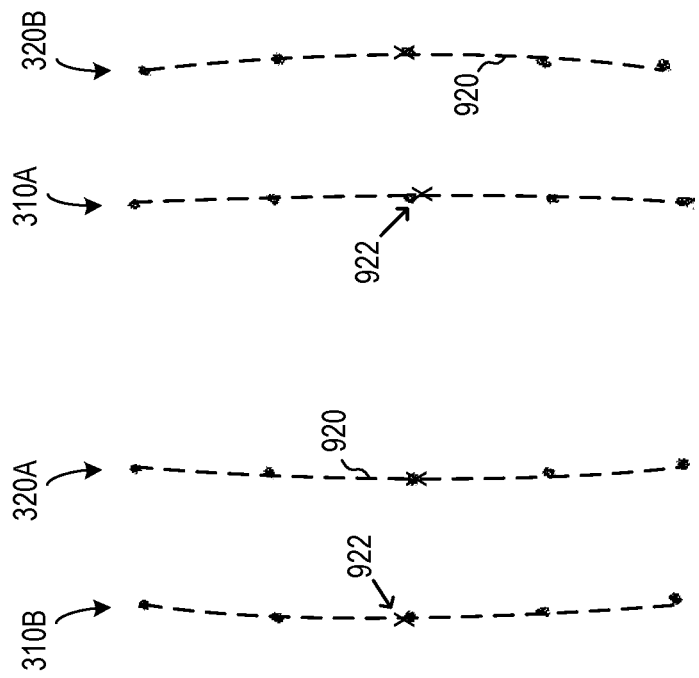
FIG. 9B depicts an exemplary technique for calculating an X-coordinate of an imaging lens centre, consistent with various embodiments of the present disclosure.
Figure 9A:
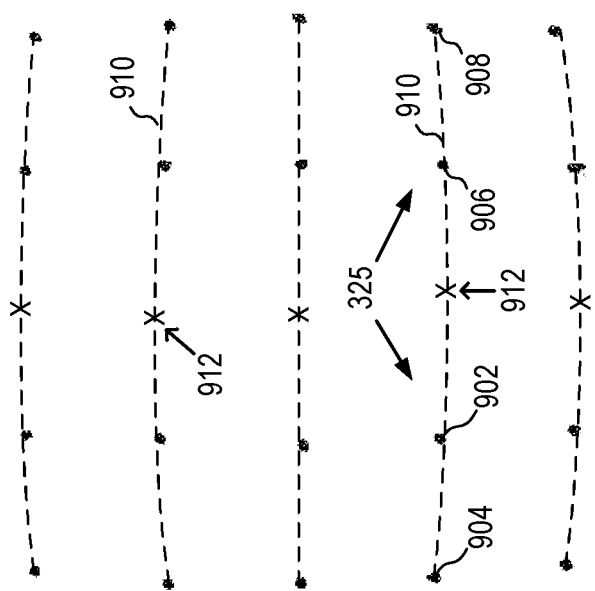
FIG. 9A depicts an exemplary technique for calculating a Y-coordinate of an imaging lens centre, consistent with various embodiments of the present disclosure.

An exemplary method of calculating the x-coordinate of the lens centre in step 802 is depicted in FIG. 9A. For each leaf pair 325 in MLC 200, controller 140 may generate a function representing a fit between the four sets of leaf position coordinates, the four sets of coordinates including the coordinates for each leaf in the retracted position and in the advanced position. For example, for leaf pair 325 depicted in FIG. 9A, position 902 may represent the position coordinates of the first leaf in the fully extended position, and position 904 may represent the position coordinates of the first leaf in the fully retracted position. Similarly, position 906 may represent the position coordinates of the second leaf in the fully extended position, and position 908 may represent the position coordinates of the second leaf in the fully retracted position. Controller 140 may generate a function 910 that represents a fit between the four points 902-908. In some embodiments, function 910 may be a second-order polynomial function. Controller 140 may generate a function 910 for each leaf pair in MLC 200. Controller 140 may then identify a maximum or minimum 912 (depending on the curvature) of each generated function 910. In some embodiments, due to the barrel distortion effect, controller 140 may identify a maximum for each leaf pair 325 above the x-axis of coordinate space 520, and a minimum for each leaf pair 325 below the x-axis of coordinate space 520. In a MLC with 80 leaves per bank, controller 140 may identify 80 maximum or minimum values 912. Controller 140 may then average the x-coordinates of all of the identified maximum or minimum values 912 to determine the x-coordinate of the lens centre.

In some embodiments, controller 140 may determine if the identified maximum or minimum for a function 910 is found on an edge of the coordinate space 520. This may occur due to rotation of an image collected in step 502 and/or due to marker detection errors. Controller 140 may correct for the rotation and marker detection errors, recalculate the maximum or minimum of the function 910, and utilize the recalculated maximum or minimum in determining the x-coordinate of the lens centre. In some embodiments, if controller 140 determines that the calculated x-coordinate of the lens centre is more than a predetermined distance from the origin 530, controller 140 may determine that the calculated x-coordinate of the lens centre is inaccurate. In such a case, controller 140 may default the x-coordinate of the lens centre to be equal to zero.

An exemplary method of calculating the y-coordinate of the lens centre in step 802 is depicted in FIG. 9B. For each bank of leaves in each image, controller 140 may generate a function representing a fit between the position coordinates of all of the leaves in the bank. For example, in FIG. 9B, 310A may represent the position coordinates of the leaves in bank 310 when the bank is in the fully extended position, and 310B may represent the position coordinates of the leaves in bank 310 when the bank is in the fully retracted position. Similarly, 320A may represent the position coordinates of the leaves of bank 320 when the bank is in the fully extended position, and 320B may represent the position coordinates of the leaves of bank 320 when the bank is in the fully retracted position. In FIG. 9B, the leaf position coordinates of 310A (which are associated with first bank 310) may be situated to the right of the leaf position coordinates of 320A (which are associated with second bank 320) because the leaves of MLC 200 may be configured to advance beyond the midway point between banks 310, 320 when moving into their respective fully-advanced positions.

Controller 140 may generate a function 920 which represents a fit between the leaf position coordinates of all leaves in a given bank at a given position. In the example depicted in FIG. 9B, controller 140 may generate four functions 920, two for each leaf bank 310, 320. In some embodiments, function 920 may be a second-order polynomial function. Controller 140 may then identify a turning point 922 for each generated function 920. For example, turning point 922 may be the position on function 920 with the largest x-value. Controller 140 may then average the y-coordinates of all of the turning points 922 to determine the y-coordinate of the lens centre.

Controller 140 may then perform steps 804-812 to determine distortion coefficient k of the camera lens. Controller 140 may determine distortion coefficient k only utilizing the leaf position coordinates for one bank of leaves in a single image. Controller 140 may calculate input coordinates $x_{input}$ and $y_{input}$ for the tip of each leaf as follows:

$$[x_{input}, y_{input}] = [x_{measured} - x_{lens}, y_{measured} - y_{lens}]$$

where $x_{measured}$ and $y_{measured}$ are the leaf position coordinates obtained in step 510 and) $x_{lens}$ and $y_{lens}$ are the x- and y-coordinates of the lens centre determined in step 802. Controller 140 may then generate distorted coordinates $x_{distorted}$ and $y_{distorted}$ for the tip of each leaf; for each leaf, $x_{distorted}$ and $y_{distorted}$ may be set equal to $x_{input}$ and $y_{input}$, respectively.

In step 804, for each leaf in the one bank, controller 140 may determine a distorted radius $r_{distorted}$ and angle $\theta$ of the leaf tip from the origin 530 as follows:

$$r_{distorted} = \sqrt{(x_{distorted} - x_{lens})^2 + (y_{distorted} - y_{lens})^2}$$

$$\theta = \frac{(y_{distorted} - y_{lens})}{(x_{distorted} - x_{lens})}$$

In step 806, controller 140 may fit the distorted x- and y-coordinates of the leaf tips to a straight line using the root mean square method, and may calculate the slope m of the fit line. In some embodiments, the fit line may not be vertical due to, among other things, slight rotation of camera 220 relative to the collimator leaves. Controller 140 may also identify the leaf tip in the bank having an x-coordinate which is furthest from origin 530 (that is, the leaf tip with the largest x-coordinate value). This leaf may be the leaf that is least distorted by the barrel distortion, since barrel distortion tends to compress images towards the image centre. Controller 140 may store the x-coordinate of this leaf tip as a variable offset.

Controller 140 may then generate a straight line with slope m and with an x-intercept equal to offset. From this line, undistorted x- and y-coordinates for each leaf tip may be calculated by controller 140 as follows:

$$x_{undistorted} = y_{distorted} \cdot m + \text{offset}$$

$$y_{undistorted} = x_{undistorted} \cdot \cos(\theta)$$

In steps 808 and 810, based upon the undistorted x- and y-coordinates of the leaf tips, controller 140 may calculate a provisional distortion coefficient $k_{temp}$ based upon the relationship between distorted and undistorted radii of the leaves. Provisional distortion coefficient $k_{temp}$ is an approximation of the distortion coefficient of the lens of camera 220. In some embodiments, controller 140 may execute a recursive function which recalculates $k_{temp}$ until an associated error value $E_k$ is determined to be below a predetermined threshold, at which time the corrected provisional distortion coefficient $k_{temp}$ may be stored as distortion coefficient k of the lens.

For each leaf, $r_{distorted}$ and $r_{undistorted}$ may be related as follows:

$$r_{distorted} = r_{undistorted} + k \cdot r_{undistorted}^3 \Rightarrow r_{distorted} - r_{undistorted} = k \cdot r_{undistorted}^3$$

Specifying this relationship only for the x-coordinate for each leaf tip, following these steps:

$$r_{distorted} - r_{undistorted} = k \cdot r_{undistorted}^3 \Rightarrow$$

$$\Rightarrow (r_{distorted} - r_{undistorted}) \cdot \cos(\theta) = (k \cdot r_{undistorted}^3) \cdot \cos(\theta)$$

Considering:

$$x_{undistorted} = r_{undistorted} \cdot \cos(\theta) \Rightarrow \cos(\theta) = \frac{x_{undistorted}}{r_{undistorted}} \quad A)$$

$$r_{undistorted} = \sqrt{x_{undistorted}^2 + y_{undistorted}^2} \quad B)$$

It follows that, for each point in a line:

$$x_{distorted} - x_{undistorted} = k \cdot r_{undistorted}^3 \cdot \cos(\theta)$$
$$= k \cdot r_{undistorted}^3 \cdot \frac{x_{undistorted}}{r_{undistorted}} =$$
$$= k \cdot r_{undistorted}^2 \cdot x_{undistorted}$$
$$= k \cdot (x_{undistorted}^2 + y_{undistorted}^2) \cdot x_{undistorted}$$
$$= k \cdot (x_{undistorted}^3 + y_{undistorted}^2 \cdot x_{undistorted})$$

Accordingly, in step 808 controller 140 may calculate a lens distortion coefficient $k_{leaf}$ for each leaf in the one bank according to the following:

$$k_{leaf} = \frac{x_{input} - x_{undistorted}}{(x_{undistorted}^3 + y_{undistorted}^2 \cdot x_{undistorted})}$$

In step 810, controller 140 may average the lens distortion coefficient $k_{leaf}$ for all of the leaves in the one bank to determine the provisional lens distortion coefficient $k_{temp}$.

Having calculated $k_{temp}$, controller 140 may calculate an error value $E_k$ associated with $k_{temp}$ and compare it to a predetermined threshold. Controller 140 may utilize $k_{temp}$ to update $r_{undistorted}$ and $r_{distorted}$ for each leaf for a subsequent iteration of the recursive function, based upon the undistorted x- and y-coordinates:

$$r_{undistorted} = \sqrt{x_{undistorted}^2 + y_{undistorted}^2}$$

$$r_{distorted} = r_{undistorted} + k_{temp} \cdot r_{undistorted}^3$$

For each leaf, controller 140 may calculate new $x_{distorted}$ and $y_{distorted}$ values based upon the following relationships:

$$r_{distorted} = \sqrt{(x_{distorted} - x_{lens})^2 + (y_{distorted} - y_{lens})^2}$$

$$\theta = \frac{(y_{distorted} - y_{lens})}{(x_{distorted} - x_{lens})}$$

The x- and y-coordinates of the lens centre ($x_{lens}$ and $y_{lens}$) and the angle $\theta$ for each leaf tip may remain constant in each iteration of the recursive function. Thus, controller 140 may utilize the updated $r_{distorted}$ value for each leaf to calculate the new $x_{distorted}$ and $y_{distorted}$ values for each leaf tip.

To determine the error $E_k$ of $k_{temp}$, controller 140 may utilize the input values and the new distorted values for the tips of the first and final leaves of the bank. Thus, in an MLC with 80 leaves per bank, controller 140 may determine $E_k$ based upon values of the first and 80$^{th}$ leaves as follows:

$$E_k = \frac{(x_{input,1} - x_{distorted,1}) + (x_{input,80} - x_{distorted,80})}{2}$$

If controller 140 determines that $E_k$ is below a predetermined threshold (e.g. less than 0.001), $k_{temp}$ may be determined to be accurate, and controller 140 may store $k_{temp}$ as the distortion coefficient k of the camera lens. However, if $E_k$ is not below the predetermined threshold, controller 140 may update the offset value as follows:

offset=offset+$E_k$

Controller 140 may utilize the updated offset value and the updated $x_{distorted}$ and $y_{distorted}$ values for each leaf to calculate new $x_{undistorted}$ and $y_{undistorted}$ values for each leaf tip. The slope m of the fit line, the x- and y-coordinates of the lens centre ($x_{lens}$ and $y_{lens}$), and the angle $\theta$, $x_{input}$, and $y_{input}$ values for each leaf may remain unchanged in each iteration. Controller 140 may repeat steps 806-810 using updated values to recalculate $k_{temp}$ until controller 140 determines that $E_k$ is less than the predetermined threshold, Controller 140 may then store $k_{temp}$ as the distortion coefficient k of the lens of camera 220. Distortion coefficient k may remain accurate until camera 220 and/or the camera lens is adjusted or replaced, or when another component of the leaf-imaging configuration, such as light projector 240 or one of mirrors 222, 224, 242, or 244 is adjusted or replaced. Such changes may affect the distortion effect, causing k to change. Accordingly, on such an occasion controller 140 may recalculate the distortion coefficient k.

Referring to step 514 in FIG. 5A, controller 140 may utilize the calculated) $x_{lens}$, $y_{lens}$, and k values to correct the optical distortion for each leaf in MLC 200. Controller 140 may calculate $r_{distorted}$ and $r_{undistorted}$ values for the tip of each leaf in MLC 200 according to the following:

$$[x_{input}, y_{input}] = [x_{measured} - x_{lens}, y_{measured} - y_{lens}]$$

$$r_{distorted} = \sqrt{(x_{input} - x_{lens})^2 + (y_{input} - y_{lens})^2}$$

$$r_{distorted} = r_{undistorted}(1 + k \cdot r_{undistorted}^2) = r_{undistorted} + k \cdot r_{undistorted}^3$$

where $x_{measured}$ and $y_{measured}$ are the leaf position coordinates obtained in step 510. Controller 140 may solve these equations to determine the undistorted radius $r_{undistorted}$ for each leaf tip. Controller 140 may also calculate an angle $\theta$ for each leaf tip, which may be the same for both the distorted and undistorted position coordinates, as follows:

$$\theta = \operatorname{atan}\left(\frac{y_{distorted}}{x_{distorted}}\right)$$

Controller 140 may determine undistorted x- and y-coordinates ("corrected leaf position coordinates") for each leaf tip as follows:

$$x_{undistorted} = r_{undistorted} \cdot \cos(\theta)$$

$$y_{undistorted} = r_{undistorted} \cdot \sin(\theta)$$

The corrected leaf position coordinates $x_{undistorted}$ and $y_{undistorted}$ may represent the true x- and y-position coordinates of each leaf tip within coordinate space 520, having been corrected to account for the optical distortion of camera 220.

In step 514, controller 140 may additionally recalculate the minor offset for each leaf by determining a distance, along the x-axis, between the imaging marker x-coordinate and $x_{undistorted}$. In some embodiments, controller 140 may calculate the minor offset for the leaf in the retracted position and for the leaf in the advanced position, and may average the two values to generate a corrected minor offset value. Advantageously, this recalculation may produce a more accurate measurement of the minor offset of each leaf because controller 140 has corrected for the optical distortion of camera 220.

In step 516, controller 140 may store the corrected minor offset values of the leaves in memory 142. In future sessions, controller 140 may receive the corrected minor offset values from the memory 142 and utilize them, for example, to control leaf placement during a radiotherapy session. The corrected minor offset values may remain accurate until a leaf of MLC 200 and/or an imaging marker 342 is replaced. In such an occasion, controller 140 may recalculate the minor offsets and store them in memory as the corrected minor offset values. Distortion coefficient k need not be recalculated when a leaf of MLC 200 or an imaging marker 342 is replaced because the optical characteristics of the camera lens remains unchanged.

In step 518, controller 140 may control movement of the leaves utilizing the corrected leaf position coordinates and/or the corrected minor offset values. For example, controller 140 may advance a leaf to a desired position based upon the corrected position coordinates of that leaf. Because $x_{undistorted}$ and $y_{undistorted}$ are known for each leaf, controller 140 may accurately determine the distance to move each leaf to achieve a desired leaf position, without inadvertently over- or under-advancing the leaf. Additionally or alternatively, controller 140 may utilize the corrected minor offsets to accurately place the tip of each leaf based upon the detected marker position. Advantageously, controller 140 may place each leaf tip in a desired position, thus forming the correct shaping window for a radiotherapy beam. In some embodiments, controller 140 can control the MLC (step 518) prior to storing the corrected minor offsets in memory (step 516).

Figure 5C:
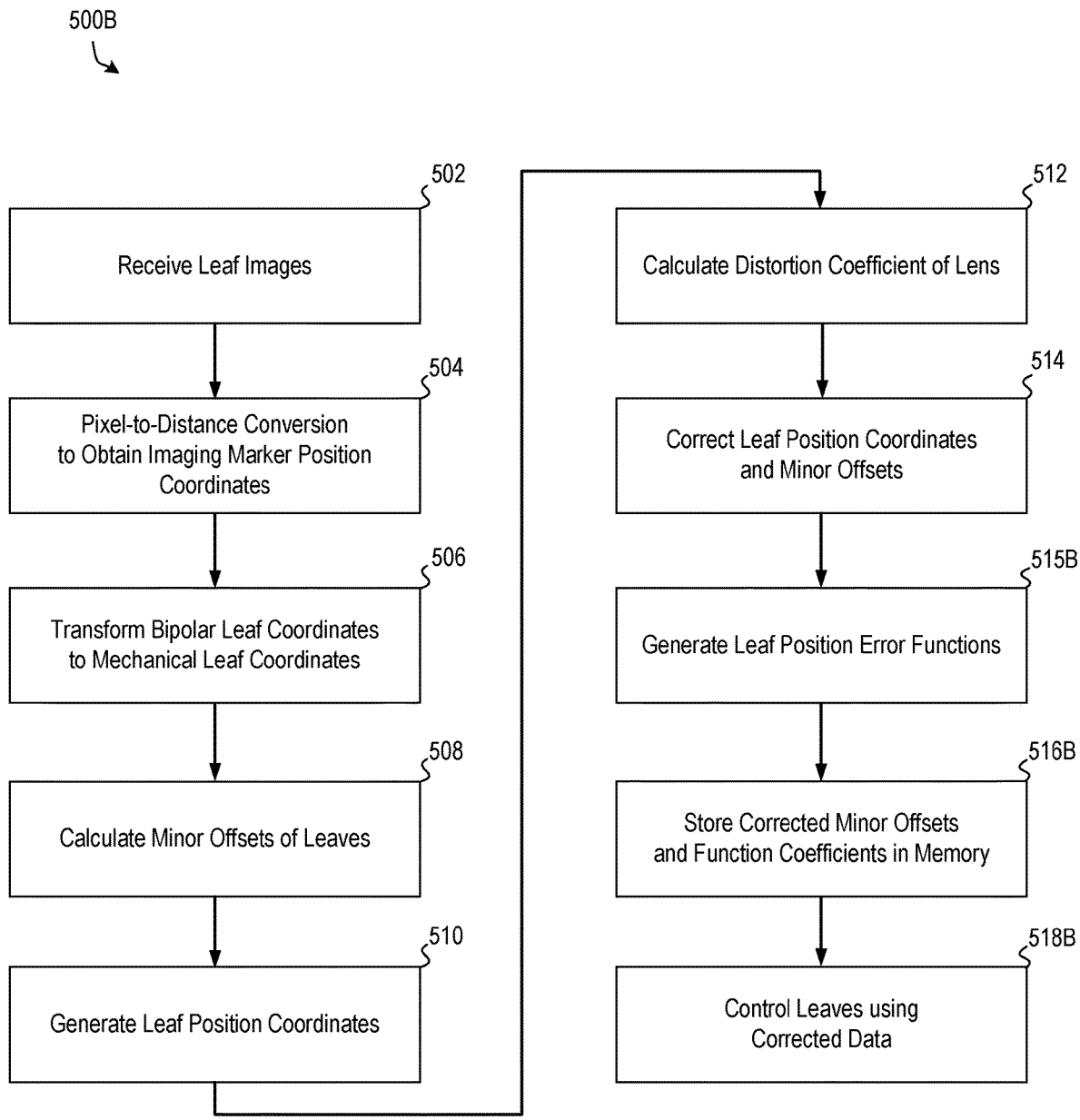
FIG. 5C is a flow diagram of another exemplary calibration method for a multi-leaf collimator, consistent with various embodiments of the present disclosure.
Figure 10:
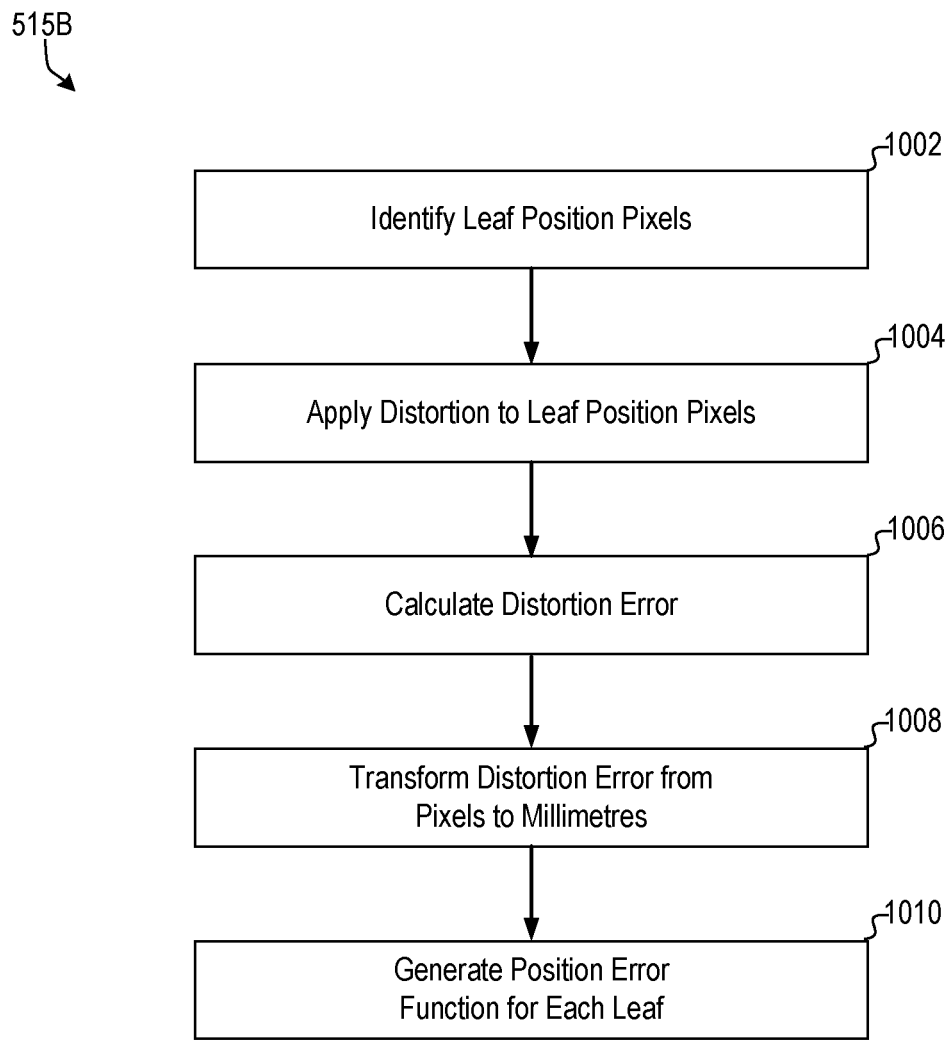
FIG. 10 is a flow diagram of an exemplary method of calculating a distortion error function for each leaf of a multi-leaf collimator, consistent with various embodiments of the present disclosure.

FIG. 5C illustrates another exemplary calibration method 500B for a multi-leaf collimator, such as MLC 200. Method 500B may also be a processor-executed method. In some embodiments, method 500B may be executed by controller 140. In method 500B, controller 140 may execute steps 502-514 of method 500A. In step 515B, controller 140 may generate a leaf position error function for each leaf in MLC 200. A leaf position error function may characterize the optical distortion of each leaf in MLC 200 by the lens of camera 220; that is, a position error function may characterize the spatial relationship between the distorted and undistorted positions of the imaging marker of each collimator leaf. Referring to FIG. 10, in step 1002, controller 140 may identify at least two positions, in pixels, for the leaves. For example, controller 140 may identify a fully retracted and a fully extended position for each leaf. Alternatively, controller 140 may identify two or more alternative positions for each leaf. In step 1004, controller 140 may apply distortion to the identified positions for each leaf. The distortion may be based, at least in part, on the characteristics of the lens of camera 220. In step 1006, controller 140 may calculate the error, along a travel direction of the leaf, between the distorted and undistorted positions for each leaf. The travel directions of the leaves may be parallel to the x-axis in FIG. 5B, as the leaves of MLC 200 may only be configured for one-dimensional advancement and retraction in the x-direction. In step 1008, controller 140 may convert the calculated error from pixels into a unit of distance (e.g. millimeters or microns) using the predetermined conversion factor discussed above, which may be constant for all leaves of MLC 200. In step 1010, controller 140 may generate a position error function for each leaf by fitting a function to the converted error. In some embodiments, the position error function may be a third order polynomial function. The position error function for each leaf may receive the distorted x-coordinate of the imaging marker as input and may output the longitudinal distance between the distorted and undistorted x-coordinates of the imaging marker.

In step 516B, controller 140 may store the corrected minor offset values and the position error function coefficients in memory 142. In future sessions, controller 140 may receive the corrected minor offset values and/or the position error function coefficients from the memory 142 and utilize them, for example, to control leaf placement during a radiotherapy session. The corrected minor offset values may remain accurate until a leaf of MLC 200 and/or an imaging marker 342 is replaced. In such an occasion, controller 140 may recalculate the minor offsets and store them in memory as the corrected minor offset values. The position error function coefficients may remain accurate until camera 220 and/or the camera lens is replaced, or when another component of the leaf-imaging configuration, such as light projector 240 or one of mirrors 222, 224, 242, or 244 is replaced.

In step 518B, controller 140 may utilize the corrected minor offsets and position error functions to accurately determine the leaf positions and to control movement of the leaves. For example, controller 140 may receive imaging marker position data from camera 220 and may utilize the position error functions to determine the true positions of the imaging markers. Controller 140 may then use the corrected minor offset values to determine the positions of leaf tips 304 and may move the tips to desired beam-shaping positions. Advantageously, controller 140 may place each leaf tip in a desired position, thus forming the correct shaping window for a radiotherapy beam.

Advantageously, the calibration methods of the present disclosure may accurately quantify and correct for the barrel distortion of camera 220 and the manufacturing inconsistencies of the minor offsets in a shorter period of time and with fewer computing steps than prior calibration methods. As a result, accurate control of the collimator leaf positions may be achieved while also reducing the length of time and the number of steps required to calibrate the MLC and to execute a radiotherapy session. This may be particularly beneficial to research hospitals and smaller clinics which may not have available time to perform radiation-based calibration.

Figure 11A:
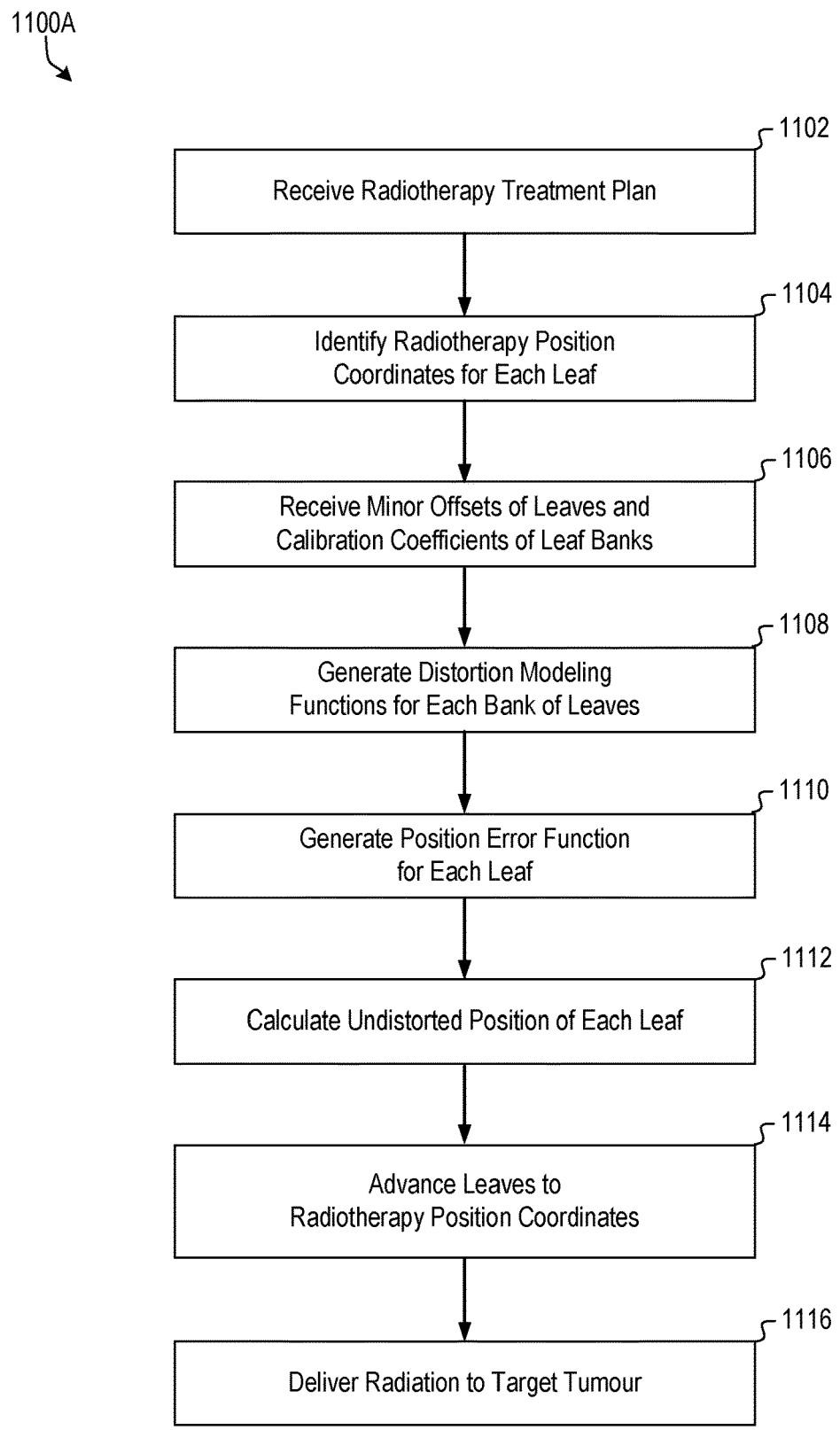
FIG. 11A is a flow diagram of an exemplary radiotherapy method, consistent with various embodiments of the present disclosure.

FIG. 11A illustrates an exemplary radiotherapy method 1100A. Method 1100A may be a processor-executed method. In some embodiments, the steps of method 1100A may be executed by the same processor, such as controller 140. Alternatively, one or more steps of method 1100A can be executed by separate processors.

In step 1102, controller 140 may receive a radiotherapy treatment plan for treating a target tissue of a patient, such as a tumour. Controller 140 may receive the treatment plan from memory, such as memory 142. In some embodiments, controller 140 may have previously generated the radiotherapy treatment plan based upon, among other things, images of the target tissue, and may have stored the treatment plan in memory 142. In other embodiments, the radiotherapy treatment plan may be generated by a different processor and may be executed by controller 140. The radiotherapy treatment plan may include radiation dose and radiation beam shape, as well as other parameters such as beam angles, dose-histogram-volume information, the number of radiation beams to be used during radiotherapy, the dose per beam, and the like. Factors such as the location and size of the target tumour may be taken into consideration to achieve a balance between efficient treatment of the tumour (e.g., such that the tumour receives enough radiation dose for an effective therapy) and low irradiation of the healthy surrounding tissue (e.g., the healthy surrounding tissue receives as low a radiation dose as possible). One of ordinary skill in the art will appreciate that the radiotherapy treatment plan described herein is merely exemplary, and that any suitable radiotherapy treatment plan may be utilized according to the present disclosure.

In step 1104, controller 140 may determine radiotherapy position coordinates for the tip of each leaf. The radiotherapy position coordinates may be determined relative to coordinate space 520 and may represent the leaf tip positions for shaping radiation beam 122 according to the received radiotherapy treatment plan.

In step 1106, controller 140 may receive the corrected minor offset values for each leaf and a set of calibration coefficients, for example from memory 142. The calibration coefficients may be coefficients of polynomial functions which characterize the optical distortion for each leaf within a bank of leaves 310, 320. For each bank of leaves, the optical distortion may be characterized by three third-order polynomials; accordingly, controller 140 may receive 24 calibration coefficients (2 banks×3 polynomials per bank×4 coefficients per polynomial). The calibration coefficients may be generated from data received from a plurality of radiation heads, optionally including radiation head 104. All of the radiation heads may have the same model camera 220, the same type of camera lens, and the same leaf-imaging configuration (for example, the arrangement of light projector 240 and the mirrors 222, 224, 242, and 244 depicted in FIG. 2). Accordingly, the calibration coefficients may be representative of the optical distortion effects in all MLCs with the same model camera, camera lens, and leaf-imaging configuration.

In some embodiments, controller 140 may generate the calibration coefficients; in some alternative embodiments, the calibration coefficients may be generated by a separate processor. The calibration coefficients may be generated in real-time, or may be generated before execution of method 1100A and accessed (e.g. from a memory) during execution of method 1100A. A processor (e.g. controller 140) may receive the data from the plurality of radiation heads and generate the lens centre, k value, and leaf position error functions for each head (e.g. according to method 500B). The processor may perform filtering to identify and remove outlier data. Such outlier data may be due to mechanical variation or tolerance; by removing the outliers, the processor may ensure that the remaining data is more representative of the camera lens and leaf-imaging configuration. The filtered data from the plurality of radiation heads may be averaged or otherwise combined to produce representative data, which the processor may fit with functions to produce the calibration coefficients. When data is received from an additional radiation head, or when a component of system 100 (e.g. the lens of camera 220) is altered or replaced, the processor may recalculate the calibration coefficients and store them (e.g. in memory 142).

In step 1106, controller 140 may receive the calibration coefficients and in step 1108, controller 140 may use the calibration coefficients to generate three distortion-modeling functions for each bank of leaves (thus, six distortion modeling functions in total). In some embodiments, the distortion modeling functions may be third-order polynomial functions, each having four coefficients. Thus, controller 140 may receive 24 calibration coefficients in step 1106. The distortion-modeling functions may characterize the optical distortion of each leaf in the corresponding leaf bank; that is, the distortion-modeling functions may receive the number of a leaf within a bank (e.g. between 1 and 80) and may generate values that quantify the optical distortion associated with the given leaf. Advantageously, the distortion-modeling functions require far fewer coefficients than the leaf position error functions generated in step 1010: the former requires just 24 coefficients, while the later requires 480 coefficients. As a result, less memory is required to store the coefficients. In addition, the distortion modeling functions may quantify the optical distortion more accurately due to the removal of outliers during the filtering processes explained above.

For a given bank of leaves (e.g. 310 or 320), controller 140 may generate the following distortion-modeling functions:

$$a_i = A_1 \cdot i^3 - B_1 \cdot i^2 + C_1 \cdot i + D_1$$

$$b_i = A_2 \cdot i^3 - B_2 \cdot i^2 + C_2 \cdot i + D_2$$

$$c_i = A_3 \cdot i^3 - B_3 \cdot i^2 + C_3 \cdot i + D_3$$

where i is the number of a leaf within the bank (e.g. with $1 \leq i \leq 80$), $A_{1-3}$, $B_{1-3}$, $C_{1-3}$, and $D_{1-3}$ are the twelve calibration coefficients for the bank of leaves, and $a_i$, $b_i$, and $c_i$ are values which quantify the optical distortion for each leaf. Controller 140 may calculate $a_i$, $b_i$, and $c_i$ for each leaf in the bank of leaves by plugging in the leaf number i to the distortion modeling functions.

In step 1110, controller 140 may generate a position error function for each leaf of MLC 200 using the calculated $a_i$, $b_i$, and $c_i$ values. Similar to the position error functions generated in step 1010, the position error functions generated in step 1110 may characterize the error in the determined imaging marker position caused by the optical distortion of the camera lens. For a given leaf i, controller 140 may generate a leaf position error function as follows:

$$\text{opticDelta}_i = a_i \cdot x_{distorted}^3 - b_i \cdot x_{distorted}^2 + c_i \cdot x_{distorted}$$

where opticDelta$_i$ quantifies the error in the determined imaging marker position along the x-axis caused by the optical distortion (in a unit of distance such as microns) and where $x_{distorted}$ is the x-coordinate of the imaging marker (relative to coordinate space 520) as detected by camera 220. Controller 140 may generate a leaf position error function for each leaf in MLC 200, and may use the functions to generate an opticDelta$_i$ value for each leaf. The y-coordinates of the leaves may not require correction because each leaf may be fixed along the y-axis of coordinate space 520; thus, the y-position of each leaf is known at all times and need not be corrected.

In step 1112, controller 140 may calculate the undistorted x-coordinate $x_{undistorted}$ of each leaf tip (in a unit of distance such as microns) as follows:

$$x_{undistorted} = x_{distorted} - x_{MO} + \text{opticDelta}_i$$

where $x_{MO}$ is the minor offset of the leaf accessed from memory in step 1106. Thus, controller 140 may correct for the barrel distortion of the camera lens and the minor offset values, and may determine the true position of each leaf tip. In step 1114, controller 140 may advance and/or retract each leaf to its respective radiotherapy position coordinates. Because the true position of each leaf is known, controller 140 may accurately determine the distance to move each leaf to position it at the radiotherapy position coordinates, without over- or under-advancing the leaf. In step 1116, controller may control radiation head 104 to deliver radiation to the target tumour. Because the leaves of MLC 200 are accurately positioned, irradiation of healthy tissue may be minimized or eliminated while ensuring that the entire area of the target tumour is irradiated according to the radiotherapy treatment plan.

Figure 11B:
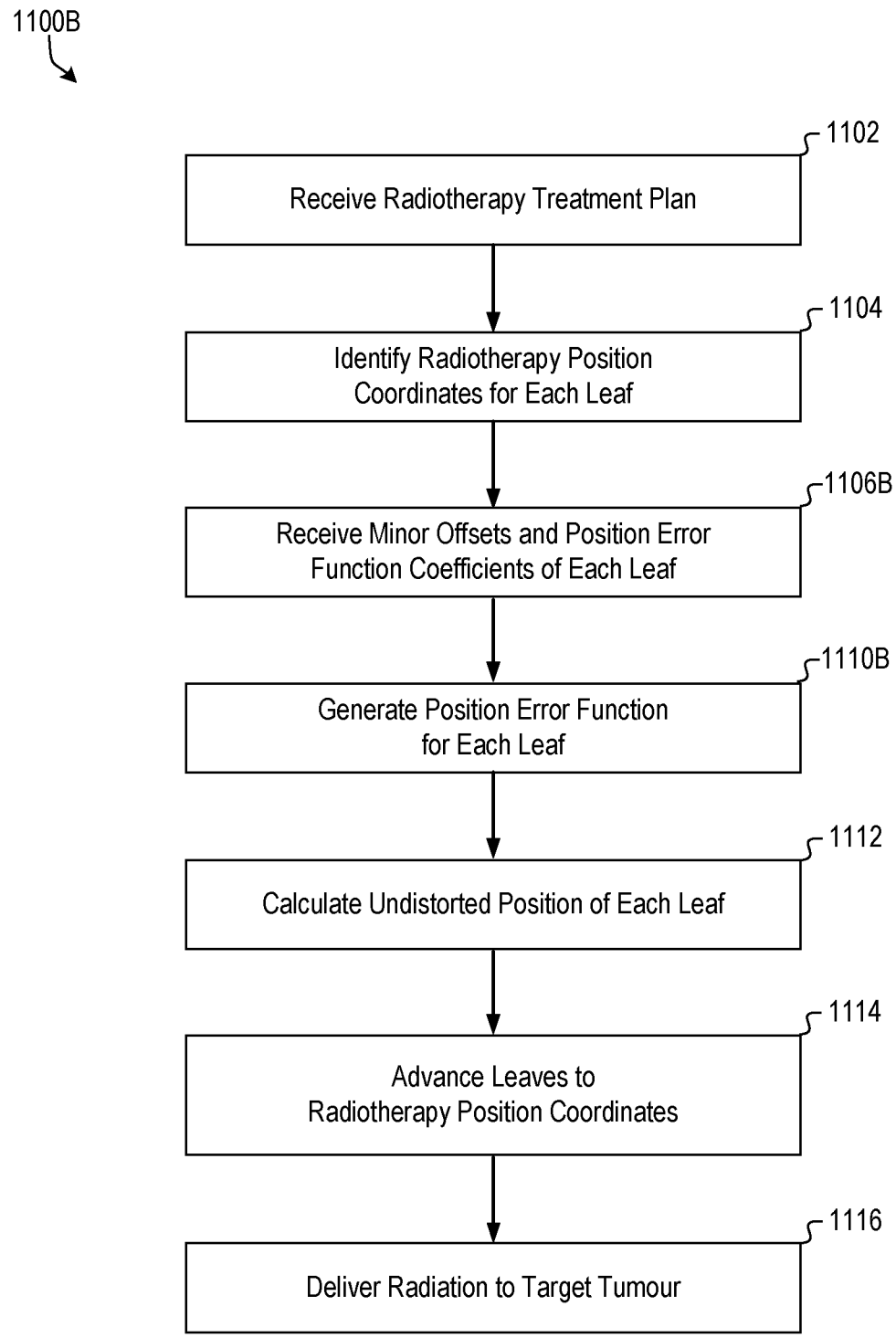
FIG. 11B is a flow diagram of another exemplary radiotherapy method, consistent with various embodiments of the present disclosure

FIG. 11B illustrates another exemplary radiotherapy method 1100B. Method 11008 may also be a processor-executed method. In some embodiments, the steps of method 1100B may be executed by the same processor, such as controller 140. Alternatively, one or more steps of method 1100B may be executed by separate processors. In method 1100B, controller 140 may execute steps 1102 and 1104 of method 1100A. In step 1106B, controller 140 may receive the corrected minor offset values of the leaves, as well as the coefficients of the leaf position error functions generated in step 1010. In step 1110B, controller 140 may regenerate the position error function for each leaf using the received coefficients. In step 1112, controller 140 may use the functions to calculate the opticDelta$_i$ value and the $x_{undistorted}$ value for each leaf. Controller 140 may execute steps 1114 and 1116 of method 1100A.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine- or computer-readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may include a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects of the invention.

Embodiments may be implemented with computer-executable instructions. The computer-executable instructions may be organized into one or more computer-executable components or modules. Embodiments may be implemented with any number and organization of such components or modules. For example, aspects of the disclosure are not limited to the specific computer-executable instructions or the specific components or modules illustrated in the figures and described herein. Other embodiments may include different computer-executable instructions or components having more or less functionality than illustrated and described herein.

When introducing elements of aspects of the disclosure or the embodiments thereof, the articles "a," "an," and "the" are intended to mean that there are one or more of the elements. The terms "comprising," "including," and "having" are intended to be inclusive and mean that there may be additional elements other than the listed elements.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. A computer-implemented method for calibrating leaves of a multi-leaf collimator of a radiotherapy device, the leaves comprising imaging markers and configured to shape a radiation beam emitted by the radiotherapy device by blocking radiation, wherein the radiotherapy device includes an imaging device configured to image the leaves, the imaging device including a lens, wherein the method comprises:

receiving, from the imaging device, a plurality of images of the leaves, wherein the leaves are in a first position in at least a first image and in a second position in at least a second image;

generating, based at least in part on the first image and the second image, initial position estimates of the leaves in the first position and in the second position, wherein the initial position estimates of the leaves are generated with respect to a predetermined coordinate space associated with the multi-leaf collimator;

determining, based at least in part on the initial position estimates of the leaves in the first position and in the second position, offsets for the leaves, the offsets reflecting differences between imaging marker positions of the leaves and positions of tips of the leaves;

identifying first position coordinates, with respect to the predetermined coordinate space, for the leaves based upon the offsets of the leaves and the initial position estimates of the leaves;

calculating a distortion coefficient of the lens based upon the first position coordinates for the leaves and the offsets of the leaves, the distortion coefficient representing an optical distortion effect associated with the lens;

determining corrected position coordinates, with respect to the predetermined coordinate space, for the leaves based on the distortion coefficient and the first position coordinates for the leaves;

correcting the offsets for the leaves based on the corrected position coordinates for the leaves; and calibrating the multi-leaf collimator based on the corrected offsets, wherein at least one leaf of the multi-leaf collimator is controlled based on the calibration.

2. The method of claim 1, wherein the multi-leaf collimator includes two banks of leaves which are captured in the images and wherein two opposing leaves constitute a leaf pair.

3. The method of claim 2, wherein the first position is a retracted position of the leaves and the second position is an extended position of the leaves.

4. The method of claim 2, wherein:
a first bank of leaves moves into the retracted position in the first image and the extended position in the second image; and
a second bank of leaves moves into the extended position in the first image and the retracted position in the second image.

5. The method of claim 2, wherein calculating the distortion coefficient comprises identifying, in the predetermined coordinate space, a lens x-coordinate and a lens y-coordinate associated with a centre of the lens.

6. The method of claim 5, wherein identifying the lens x-coordinate comprises:
for each leaf pair, generating a function based on the first position coordinates of the two opposing leaves in the first position and in the second position;
identifying one of a maximum or a minimum of each function;
determining an x-coordinate, relative to the predetermined coordinate space, of each maximum or minimum; and
averaging the x-coordinates of the maximums and minimums.

7. The method of claim 6, wherein the function of each leaf pair is a second-order polynomial.

8. The method of claim 5, wherein identifying the lens y-coordinate comprises:
for each bank of leaves in each of the first and second positions, generating a function based on the first position coordinates of the leaves;
identifying a turning point for each function; and
averaging the turning points.

9. The method of claim 8, wherein the function for each bank of leaves in each of the first and second positions is a second-order polynomial.

10. The method of claim 2, wherein calculating of the distortion coefficient of the lens comprises:
generating a function based on the first position coordinates and offsets of a selected one of the banks of leaves in one of the images;
calculating a provisional distortion coefficient of the lens based on the function;
determining an error value of the provisional distortion coefficient;
if the error value is above a predetermined threshold, regenerating the function using the error value, recalculating the provisional distortion coefficient of the lens based on the regenerated function, and determining the error value of the recalculated provisional distortion coefficient until the error value is below the predetermined threshold; and
when the error value is below the predetermined threshold, setting the distortion coefficient of the lens to be equal to the provisional distortion coefficient.

11. The method of claim 10, wherein the function is generated using a root mean square technique.

12. The method of claim 10, wherein calculating the provisional distortion coefficient comprises:
determining undistorted position coordinates, with respect to the predetermined coordinate space, for each leaf in the selected bank of leaves by minimizing, with the generated function, optical distortion associated with the lens;
calculating a distortion coefficient of each leaf in the selected bank of leaves based on the undistorted position coordinates; and
generating the provisional distortion coefficient of the lens by averaging the distortion coefficients of the leaves.

13. The method of claim 1, further comprising identifying the imaging marker positions of the leaves utilizing a predetermined conversion factor relating numbers of pixels and distance.

14. The method of claim 1, wherein determining the offsets for the leaves comprises:
identifying the imaging marker positions of the leaves, wherein each leaf is associated with at least two identified imaging marker positions;
averaging, for each leaf, the imaging marker positions;
identifying a reference leaf based on the average imaging marker positions;
determining differences between the average imaging marker positions of the leaves and the average imaging marker position of the reference leaf; and
calculating the offsets based on the determined differences.

15. A computer-implemented method for use in a radiotherapy device that emits a radiation beam to treat a target tumour of a patient, wherein the radiotherapy device comprises a multi-leaf collimator having a plurality of leaves, the leaves comprising imaging markers and configured to shape the radiation beam emitted by the radiotherapy device by blocking radiation, wherein the radiotherapy device includes an imaging device configured to image the leaves, the imaging device including a lens, wherein the method comprises:
receiving a treatment plan for treating the target tumour with radiation, wherein the treatment plan includes a therapeutic radiation beam shape for irradiating the target tumour;
identifying radiotherapy position coordinates, with respect to a predetermined coordinate space associated with the multi-leaf collimator, for the leaves of the multi-leaf collimator, wherein the leaves form the therapeutic radiation beam shape by blocking radiation when they are positioned at the radiotherapy position coordinates;
receiving offsets for the leaves, the offsets reflecting differences between imaging marker positions of the leaves and positions of tips of the leaves;

receiving calibration coefficients based on leaf position data from multiple multi-leaf collimators;

generating a position error function based on the calibration coefficients, wherein the position error function indicates a leaf position error associated with an optical distortion effect of the lens; and controlling the leaves to move to the radiotherapy position coordinates based on the offsets and the position error function.

16. The method of claim 15, wherein the multi-leaf collimator includes two opposing banks of leaves and wherein generating the position error function comprises:

generating position error polynomials for the banks of leaves, wherein each position error polynomial is based on different calibration coefficients;

receiving, from the imaging device, an image of the leaves;

identifying distorted position coordinates, with respect to the predetermined coordinate space, for the leaves based upon positions of the imaging markers of the leaves in the image; and generating the position error function based on the position error polynomials and the distorted position coordinates of the leaves.

17. The method of claim 16, wherein each bank of leaves is associated with three position error polynomials, and each position error polynomial is based on four calibration coefficients.

18. The method of claim 15, wherein the offsets of the leaves are determined, at least in part, from leaf position data obtained when the leaves are in a first position and upon leaf position data obtained when the leaves are in a second position.

19. The method of claim 15, wherein the position error function indicates a leaf position error of each leaf.

20. The method of claim 15, further comprising:

calculating corrected calibration coefficients to accommodate an adjustment of the multi-leaf collimator; and generating a corrected position error function based on the corrected calibration coefficients.

\* \* \* \* \*